United States Patent [19]

Cardin et al.

[11] Patent Number: 5,707,615

[45] Date of Patent: Jan. 13, 1998

[54] METHOD OF TREATING HIV INFECTIONS WITH ANTI-VIRAL FORMULATIONS

[75] Inventors: Alan D. Cardin; Richard L. Jackson, both of Cincinnati, Ohio; Michael J. Mullins, Midland, Mich.

[73] Assignee: Merrell Pharmaceuticals Inc., Cincinnati, Ohio

[21] Appl. No.: 834,697

[22] Filed: Apr. 1, 1997

Related U.S. Application Data

[60] Continuation of Ser. No. 444,461, May 19, 1995, abandoned, which is a division of Ser. No. 132,551, Oct. 6, 1993, Pat. No. 5,606,108, which is a division of Ser. No. 710,370, Jun. 10, 1991, Pat. No. 5,276,182, which is a continuation-in-part of Ser. No. 549,782, Jul. 9, 1990, abandoned.

[51] Int. Cl.$^6$ .................................................. A61K 31/74
[52] U.S. Cl. ................................................. 424/78.08
[58] Field of Search ................................. 514/563, 576; 424/78.08

[56] References Cited

U.S. PATENT DOCUMENTS

| | | |
|---|---|---|
| 2,833,744 | 5/1958 | Neher . |
| 3,528,949 | 9/1970 | Rutledge . |
| 4,604,404 | 8/1986 | Munson et al. . |
| 4,783,446 | 11/1988 | Neushul . |
| 4,824,916 | 4/1989 | Kershner et al. . |
| 4,895,660 | 1/1990 | Kershner . |
| 4,966,894 | 10/1990 | Herr et al. . |
| 5,424,063 | 6/1995 | Cardin et al. . |

FOREIGN PATENT DOCUMENTS

| | | |
|---|---|---|
| 0232744 | 8/1987 | European Pat. Off. . |
| 0498095 | 2/1991 | European Pat. Off. . |
| 0467185 | 1/1992 | European Pat. Off. . |
| 2669535 | 5/1992 | France . |
| 90/0094 | 10/1990 | South Africa . |
| 0781479 | 8/1957 | United Kingdom . |
| 0907829 | 10/1962 | United Kingdom . |
| 8800828 | 2/1988 | WIPO . |
| 9200749 | 1/1992 | WIPO . |
| 9314146 | 7/1993 | WIPO . |
| 9316992 | 9/1993 | WIPO . |

OTHER PUBLICATIONS

Vandenberg E.J. et al., Polymeric Materials Science and Engineering vol. 57, Fall Meeting, 1987, pp. 139–143.

R.M. Ottenbrite, ACS Symposium Series #186, pp. 205–220 (1982) "The Antitumor and Antiviral Effects of Polycarboxyl–ic Acid Polymers".

European Chem. News, p. 17 (Jul. 30, 1990).

Ahmed, et al., Antiviral Chemistry & Chemotherapy, (1995) 6(1), 34–42, "Potent Inhibition of Herpes Simplex Virus by MDL101028" a Novel Biphenyl Disulphonic Acid Co–polymer.

Antiviral Research, 18(1992), Sulfonic acid polymers as a new class of human immunodefic–ciency virus inhibitors, Prem Mohan, et al., pp. 139–150.

Komp et al, Chemical Abstracts vol. 110 Abstract No. 33727k (1989).

Cardin et al. "Stilbene Disulfonic Acids. CD4 Antagonists that Block human immunodeficiency Virus Type–1 Growth at Multiple Stages of the Viral like Cycle" J. Biol. Chem (1991), 266(20), 13355–63.

Hofferek et al., Chemical Abstracts vol. 114: 180333q (1990).

Taylor et al, "Potent Inhibition of Human Immunodeficiency Virus (HIV) by MDL 101028", a Novel Supphonic Acid Polymer.

Antiviral Research, 18 (1992), Sulfonic acid polymers as a new class of human immunodefi–ciency virus inhibitors, Prem Mohan, et al., pp. 138–150.

Primary Examiner—Raymond Henley, III
Attorney, Agent, or Firm—Stephen L. Nesbitt

[57] ABSTRACT

The preferred oligomers of the present invention are polyureas, polycarbonates, polyesters or polyamides having a number average molecular weight of <10,000. These oligomers are water-soluble, have a rigid backbone, have recurring units coupled by carbonyl linking moieties which have anionic groups, display predominantly linear geomentry such that regular spacing between anionic groups exists in an aqueous medium, and are pharmaceutically-acceptable. The oligomers are useful for the treatment and/or diagnosis of AIDS and ARC.

25 Claims, No Drawings

METHOD OF TREATING HIV INFECTIONS WITH ANTI-VIRAL FORMULATIONS

CROSS-REFERENCE TO RELATED APPLICATION

This is a continuation of application Ser. No. 08/444,461, filed May 19, 1995, now abandoned, which is a division of Ser. No. 08/132,551, filed Oct. 6, 1993, now U.S. Pat. No. 5,606,108,; which is a division of application Ser. No. 07/710,370, filed Jun. 10, 1991 now U.S. Pat. No. 5,276,182; which is a continuation-in-part of Ser. No. 07/549,782, filed Jul. 9, 1990, now abandoned, which is herein incorporated by reference.

This invention concerns oligomers, their uses and formulations, as well as processes for their preparation. The present oligomers are anionic compounds that have particularly valuable anti-human immunodeficiency virus activity and these oligomers are thus useful in the treatment of acquired immune deficiency syndrome (AIDS).

BACKGROUND OF THE INVENTION

A great deal of research is currently underway to develop treatments and cures for viral infections in humans and in animals. Notably the incidence of AIDS and AIDS related complex (ARC) in humans is increasing at an alarming rate. The five year survival rate for those with AIDS is dispiriting and AIDS patients, whose immune systems have been seriously impaired by the infection, suffer from numerous opportunistic infections including *Kaposi's sarcoma* and *Pneumocystis carinii pneumonia*. No cure for AIDS is known and current treatments are largely without adequate proof of efficacy and have numerous untoward side effects. Fear of the disease has resulted in social ostracism of and discrimination against those having or suspected of having the disease.

Retroviruses are a class of ribonucleic acid (RNA) viruses that replicate by using reverse transcriptase to form a strand of complementary DNA (cDNA) from which a double stranded, proviral DNA is produced. This proviral DNA is then randomly incorporated into the chromosomal DNA of the host cell making possible viral replication by later translation of viral message from one integrated viral genome.

Many of the known retroviruses are oncogenic or tumor causing. Indeed, the first two human retroviruses discovered, denoted human T-cell leukemia viruses I and II or HTLV-I and II, were found to cause rare leukemias in humans after infection of T-lymphocytes. The third such human virus to be discovered, HTLV-III, now referred to as HIV, was found to cause cell death after infection of T-lymphocytes and has been identified as the causative agent of AIDS and ARC.

The envelope protein of HIV is a 160 kDa glycoprotein. The protein is cleaved by a protease to give a 120 kDa external protein, gp120, and a transmembrane glycoprotein, gp41. The gp120 protein contains the amino acid sequence that recognizes the CD4 antigen on human T-helper (T4) cells.

One approach being explored is to prevent the binding of HIV to its target, the T4 cells in humans. These T4 cells have a specific region, a CD4 antigen, which interacts with gp120. If this interaction can be disrupted, the host cell infection can be inhibited.

Interference with the formation of the viral envelope glyoprotein could prevent the initial virus-host cell interaction or subsequent fusion or could prevent viral duplication by preventing the construction of the proper glycoprotein required for the completion of the viral membrane. It has been reported [See H. A. Blough et al., *Biochem. Biophys. Res. Comm.* 141(1), 33–38 (1986)] that the nonspecific glycosylation inhibitors 2-deoxy-D-glucose and β-hydroxynorvaline inhibit expression of HIV glycoproteins and block the formation of syncytia. Viral multiplication of HIV-infected cells treated with these agents is stopped, presumably because of the unavailability of glycoprotein required for the viral membrane formation. In another report [W. McDowell et al., *Biochemistry* 24(27), 8145–52 (1985)], the glycosylation inhibitor 2-deoxy-2-fluoro-D-mannose was found to inhibit antiviral activity against influenza infected cells by preventing the glycosylation of viral membrane protein. This report also studied the antiviral activity of 2-deoxyglucose and 2-deoxy-2-fluoroglucose and found that each inhibited viral protein glycosylation by a different mechanism. However, other known glycosylation inhibitors have been shown to have no antiviral activity. Thus the antiviral activity against viruses in general, and the viral activity specifically, of glycosylation inhibitors is quite unpredictable.

It has been disclosed in U.S. application Ser. No. 295,856, filed Jan. 11, 1989, that a purified form of heparin, a sulfated polysaccharide, binds through interactions to a viral protein which is responsible for cell recognition and provides limited inhibition of host cell infection. However, heparin causes some side effects, notably hemorrhage and increased clot formation time as well as thrombocytopenia. Use of heparin is contraindicated in patients who are actively bleeding, or have hemophilia, purpura, thrombocytopenia, intracranial hemorrhage, bacterial endocarditis, active tuberculosis, increased capillary permeability, ulcerative lesions of the gastrointestinal tract, severe hypertension, threatened abortion or visceral carcinoma. The contraindication for use by hemophiliacs is particularly of concern because many such individuals are now HIV positive.

It has long been recognized that certain synthetic, water-soluble polymers exhibit a broad spectrum of biological activity [R. M. Ottenbrite in "Biological Activities of Polymers", *Amer. Chem. Soc. Symp.* Ser. No. 182, pp. 205–220, eds. C. E. Carraher and C. G. Gebelein (1982)]. A copolymer of divinyl ether and maleic anhydride has been shown to be active against a number of viruses and its use in cancer chemotherapy has been studied for years [Breslow, D. S. *Pure and Applied Chem.* 46, 103 (1976)]. Polyacrylic, polymethacrylic and a variety of other aliphatic backbone water soluble polymers also have been shown to have a broad spectrum of biological activities [W. Regelson et al., *Nature* 186, 778 (1976)]. Unfortunately, the extreme toxicity of these polymers has prevented their clinical use. Also, these polymers have a high molecular weight and are unable to pass through the renal membranes.

Attempts have been made to circumvent the toxicity and excretion problems by synthesis of low molecular weight (1,000 to 10,000) aliphatic polymers [R. M. Ottenbrite in "Biological Activities of Polymers", *Amer. Chem. Soc. Symp.* Ser. No. 182, pp. 205–220, eds. C. E. Carraher and C. G. Gebelein (1982)]. It has been found that such polymers are less toxic but have much reduced antiviral activity. These low molecular weight aliphatic polymers may be classed as "random coil" polymers. Such polymers have an unpredictable configuration because of the flexibility of the backbone linking groups. The configuration of random coil polymers in solution may be generally described as globular. Although the mechanism of action of such water-soluble polymers is unknown, one postulate is that the polymer binds to the viral membrane, e.g. encephelomyocarditis, through an ionic attraction, thus rendering the virus unable to infect host cells.

An additional synthetic polymer approach is to place ionic groups on the backbone of a polymer which exhibits a more defined geometry. There are numerous examples of non-ionic, synthetic polymers which exhibit a more linear geometry in non-aqueous solution than do the aliphatic polymers described above [*J. Macromoecular Sci-Reviews in Macromol. Chem. Phys.* C26(4), 551 (1986)]. The factors involved which cause this non-random coil structure are complex and poorly understood. In general, such polymers have either a very limited number of rotatable bonds which are not parallel to the polymer axis, or there is hydrogen bonding or dipolar interactions which favor linear structures. These polymers are referred to as having a "rigid backbone". A polyamide derived from terephthalic acid and p-diaminobenzene (known commercially as Kevlar™ supplied by DuPont) is a well-known example of such polymers.

Synthetic, water-soluble, rigid polymers are much less common, but a few high molecular weight examples are known (e.g. see U.S. Pat. Nos. 4,824,976 and 4,895,660). The non-random coil structure of this class of polymer results in high solution viscosities for a given molecular weight and concentration.

Clearly, it would be desirable to find a treatment and cure for AIDS and ARC which would display minimal or no side effects and constitute a clear improvement over the polymers previously employed as a pharmaceutical.

SUMMARY OF THE INVENTION

It has now been discovered that anionic oligomers inhibit viral replication without the side effects shown by heparin and known polymers. The oligomers have an ordered anion spacing, have a rigid backbone and are water-soluble.

The novel oligomers of the present invention are anionic, carbonyl containing compounds. Examples of such oligomers are polyureas, polycarbonates, polyesters or polyamides having a number average molecular weight, $M_n$, of <10,000 which are water-soluble, have a rigid backbone, and have an ordered anion spacing. The oligomers include their salts, which are pharmaceutically-acceptable when used as pharmaceutical agents.

Other uses for these anionic oligomers are as effective thickening agents in aqueous solutions, or as mild ionic detergents. In general, water soluble polymers, including those oligomers of the present invention, have a wide spectrum of uses as thickeners, dispersants, and flocculants. The present oligomers may be used in applications for oil fields, mining, paper manufacturing, textile manufacturing, cosmetic ingredients and manufacturing, and food processing. Additionally the present low molecular weight polymers, i.e. oligomers, may be used as starting materials for the preparation of high molecular weight polymers and copolymers.

Thus, this invention concerns a water-soluble, rigid backbone oligomer having a molecular weight less than (<) 10,000 comprising recurring units coupled by carbonyl linking moieties, said oligomer having anionic groups and predominantly linear geometry such that regular spacing between anionic groups exists in an aqueous medium. Preferably each recurring unit has at least two anionic groups.

Any oligomer which meets the above criteria can be used in this invention. Particularly preferred oligomers are those which are polyureas, polycarbonates, polyesters or polyamides. These oligomers preferably assume a linear geometry.

DETAILED DESCRIPTION OF THE INVENTION

The novel oligomers of the present invention are illustrated by polyureas, polycarbonates, polyesters or polyamides having a number average molecular weight $M_n$ of 10,000 which are water-soluble, have a rigid backbone, have an ordered anion spacing and a predominantly linear geometry in an aqueous medium. The oligomers are preferably linear in their backbone and also may be in their salt form, particularly preferred salts are those that are pharmaceutically-acceptable.

The preferred oligomers of this invention are represented by any one of the following formulae:

A) a polyurea of the formula:

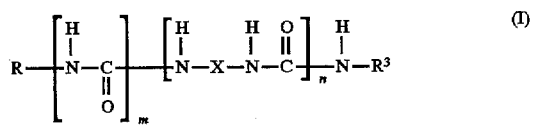

wherein:

R represents a hydrogen atom, a $C_1$-$C_4$ alkyl group, a phenyl group, or a phenyl group substituted with from 1 to 2 $R^1$ moieties and up to 3 substituents independently selected from a chloro or bromo atom or $C_1$-$C_4$ alkyl group;

$R^1$ represents —$SO_3R^2$, —$CO_2R^2$, —$PO_3(R^2)_2$, or —$OPO_3R^2$;

$R^2$ represents a hydrogen atom or a pharmaceutically-acceptable cation;

m is an integer 0 or 1, with the proviso that when m is 0, R is a hydrogen atom;

X represents

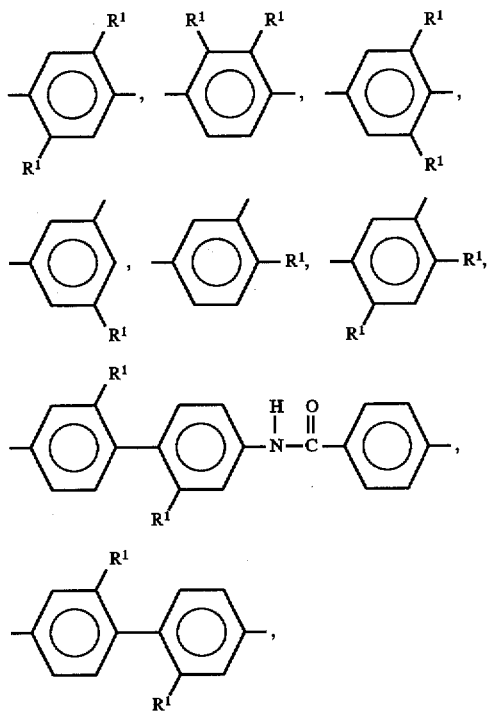

-continued

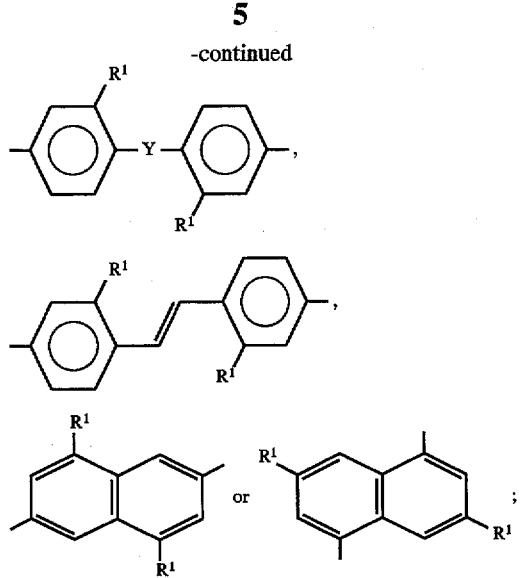

Y represents —CO₂—, —C≡C—, —N=N—,

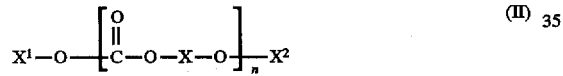

n is an integer from 3 to 50; and
R³ represents —R or —X—NH₂, where R and X are defined as before;

B) a polycarbonate of the formula:

$$X^1-O\left[\begin{matrix}O\\\|\\C-O-X-O\end{matrix}\right]_n X^2 \quad (II)$$

wherein;

X and n are defined as in Formula I above;

X¹ represents a HO—X— group, where X is defined as for Formula I above, or a C₁–C₄ alkyl group, a phenyl group, or a phenyl group substituted with from 1 to 2 R¹ moieties and up to 3 substituents independently selected from a chloro or bromo atom or C₁–C₄ alkyl group; and X² represents a hydrogen atom, or —CO₂X¹, where X¹ is defined as above;

C) a polyester of the formula $$R^4O\left[\begin{matrix}O&&O\\\|&&\|\\C-X^3-C-O-X-O\end{matrix}\right]_n R^5 \quad (III)$$

wherein:

X and n are defined as in Formula I above;

R⁴ represents —R², as defined in Formula I, or —X¹, as defined in Formula II above;

R⁵ represents

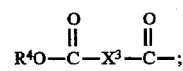

where

R⁴ is defined as in Formula III above, or —R², where

R² is defined as in Formula I above;

X³ represents

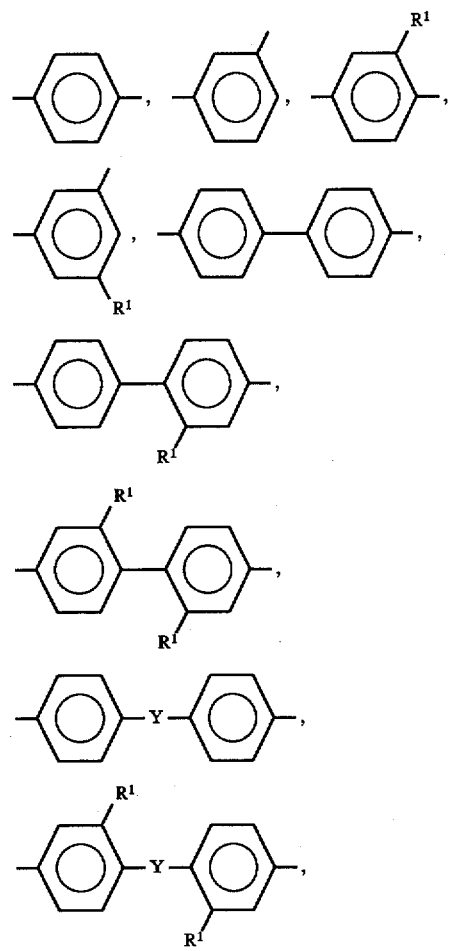

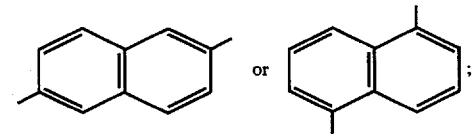

wherein

R¹ and Y are defined as in Formula I above; or

D) a polyamide of the formula:

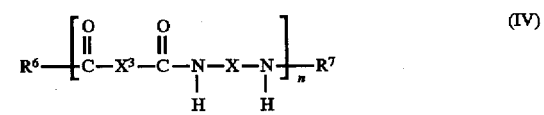

wherein:

X and n are defined as in Formula I above;

X³ is defined as in Formula III above;

R⁶ represents H₂N—X—NH—, R²O—, RNH— or R—C(O)—NH—X—NH—, where R, R² and X are defined as in Formula I;

R⁷ represents a hydrogen atom,

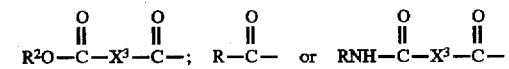

where

R and R² are defined as in Formula I above; and $X^3$ is defined as in Formula III above.

The term "pharmaceutically-acceptable cation" means a cation acceptable for pharmaceutical use. Those cations that are not substantially toxic at the dosage administered to achieve the desired effect and do not independently possess significant pharmacological activity are included within the term "pharmaceutically-acceptable cation". Illustratively, these salts include those of alkali metals, such as sodium and potassium; alkaline earth metals, such as calcium and magnesium; ammonium; light metals of Group IIIA including aluminum; and organic primary, secondary and tertiary amines, such as trialkylamines, including triethylamine, procaine, dibenzylamine, N,N'-dibenzylethylenediamine, dihydroabietylamine, N—($C_1$–$C_4$)alkylpiperidine, and any other suitable amine. Sodium and potassium salts are preferred. The term "pharmaceutically-acceptable" means suitable for administration to warmblooded animals, especially human beings, and includes being nontoxic, e.g. suitable for pharmaceutical use and is not poisonous to the warmblooded animal. The pharmaceutically-acceptable cations of the oligomers of the present invention are prepared by conventional ion exchange processes or by treating the $R^1$ acid with an appropriate base.

When uses other than for pharmaceuticals are the object for the present oligomers, then salts that would otherwise not be as acceptable for pharmaceutical uses may be employed. Examples of such additional salts include barium, zinc and titanium.

The oligomers of the present invention are low molecular weight, rigid backbone, water-soluble polymers. Additionally, the oligomers have ordered anion spacing. By "ordered anion spacing" or "regular spacing between anionic groups" is meant that the anionic groups ($R^1$) are present in the backbone of the polymer at intervals determined by the starting material reagent used and the occurrence of the anionic groups is controlled in a predictable manner. While not wishing to be bound by any theory, the anionic groups of the oligomers are believed to be the portion that binds to the HIV and/or cell membrane and thereby interrupts the ability of the virus to replicate.

The terms "predominantly linear geometry" in an aqueous medium refers to the solution configuration of the oligomer. A method well known in the art for characterization of the solution configuration of polymer molecules is based on the following formula, referred to as the Mark-Houwink equation ["Introduction to Physical Polymer Science", ed. L. H. Sperling, pub. John Wiley & SONS (1985), pp. 81–83], $$[\eta] = KM^\alpha$$

wherein $\eta$ is intrinsic viscosity; M is weight average molecular weight; K is a constant related to chain bond dimension; and $\alpha$ is a constant determined by polymer configuration. The intrinsic viscosity ($\eta$) for a random coil polymer is $0.5 < \alpha < 0.9$; and for a linear polymer is $0.9 \le \alpha < 1.8$. This formula relates the solution viscosity "$\eta$" to the molecular weight "M". For this invention linear polymers are defined as having "$\alpha$" values greater than or equal to 0.9. For a rigid rod polymer the theoretical upper limit is 1.8. For a given molecular weight a higher solution viscosity will be obtained from polymers with a linear configuration relative to those polymers which exist as a random coil. An additional consideration is that the "$\alpha$" value is a function of the solvent used. The "$\alpha$" for a given water soluble polymer may be different at different salt concentrations. For this invention, the salt concentration is set at the levels present in serum (approximately 80 g/L NaCl, 4 g/L KCl).

As used herein, the term "oligomer" encompasses all the possible values for n, e.g., 3 through 50. The oligomers are preferably linear with n equal to an integer from 3 to 50, preferably from 3 to 20, more preferably from 3 to 15. Of course, the n value is directly related to the molecular weight of the resulting oligomer. It is essential that these oligomers are of sufficiently low molecular weight in order to pass through the renal excretory membrane, but able to inhibit the HIV virus. The average molecular weight is governed by the stoichiometry of the reagents. The number average molecular weight ($M_n$) is <10,000, preferably from about 500 to about 10,000, and most preferably from about 1,000 to about 6,000.

For the purpose of the present invention, the oligomers described herein and physiologically-acceptable salts thereof are considered equivalent. Physiologically-acceptable salts refer to the salts of those bases which will form a salt with at least one acid group of the $R^1$ group and which will not cause significant adverse physiological effects when administered as described herein. Suitable bases include, for example, the alkali metal and alkaline earth metal hydroxides, carbonates, and bicarbonates such as sodium hydroxide, potassium hydroxide, calcium hydroxide, potassium carbonate, sodium bicarbonate, magnesium carbonate and the like, ammonia, primary, secondary and tertiary amines and the like. Particularly preferred bases are the alkali metal hydroxides, carbonates, and bicarbonates. Physiologically-acceptable salts may be prepared by conventional ion exchange processes or by treating the $R^1$ acid with an appropriate base. Examples of additional salts have been described herein.

The formulations of the present invention are in the solid or liquid form. These formulations may be in kit form such that the two components are mixed at the appropriate time prior to use. Whether premixed or as a kit, the formulations usually require a pharmaceutically-acceptable carrier or adjuvant.

The oligomers of the present invention are soluble in water and in salt solutions, especially at physiological pH and in saline solutions. Thus the present oligomers are readily formulated into a suitable aqueous pharmaceutical dosage form. Also, after the present oligomer formulation is administered, the oligomer remains soluble in vivo.

Preferred terms for the previously described Formulae 1 to IV are as follows:

R and $R^3$ are a 4-methylphenyl group;

m is 1;

n is 3 to 15;

$R^4$ and $R^5$ are hydrogen;

$R^6$ is phenyl;

$R^7$ is benzoyl;

$X^1$ is a 4-methylphenyl group;

$X^2$ is —$CO_2$-(4-methylphenyl) group;

$X^3$ represents

,

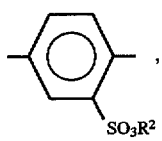,

-continued

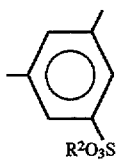

or

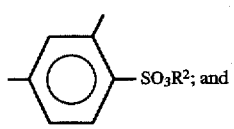

X represents

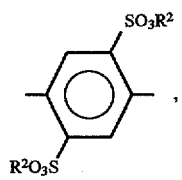,

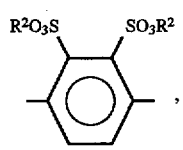,

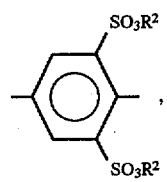,

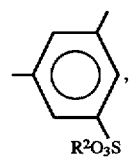,

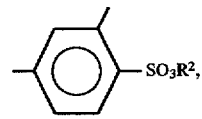,

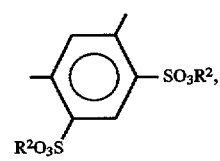,

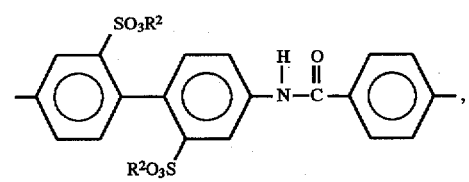,

-continued

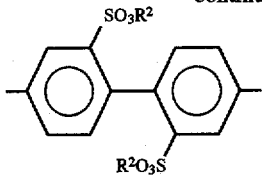

or

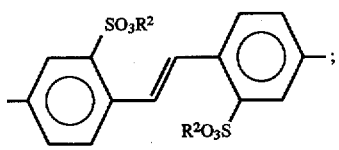;

while especially preferred is

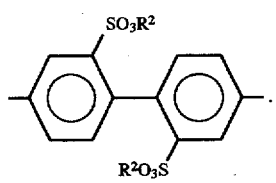.

Anti-HIV anionic oligomers can be used to prevent syncytium formation in cells infected with HIV-I virus or other related viruses having gp120 surface protein. Anti-HIV anionic oligomers can be used to treat AIDS and ARC and other diseases caused by the retrovirus HIV-I or other related viruses having gp120 surface protein. The anionic oligomers of this invention can be used as a pure compound, or as mixtures, such as those of n values of a particular Formula I to IV, or mixtures of more than one Formula, e.g., Formula I with Formula II compounds, or as mixtures with other known agents for the present anti-viral utilities. However, for all oligomers prepared, n represents the number average repeat length of the distribution through all formulae.

The amount of anti-HIV anionic oligomers which is needed to prevent syncytium formation in HIV infected cells can be any effective amount. Experimentally, it has been determined that anti-HIV anionic oligomers, when employed at a concentration of 10 µg/mL of aqueous formulation, resulted in complete inhibition of syncytium formation as well as reduced the presence of p24 antigen, an indicator of viral replication, to below 300 pg/ml. The amount of anti-HIV anionic oligomers to be administered in order to treat AIDS or ARC or other disease caused by HIV infection can vary widely according to the particular dosage unit employed, the period of treatment, the age and sex of the patient treated, the nature and extent of the disorder treated, and other factors well-known to those practicing the medical arts. Moreover anti-HIV anionic oligomers can be used in conjunction with other agents known to be useful in the treatment of retroviral diseases and agents known to be useful to treat the symptoms of and complications associated with diseases and conditions caused by retroviruses.

The anti-HIV effective amount of anti-HIV anionic oligomers to be administered according to the present invention will generally range from about 0.1 mg/kg to 500 mg/kg of body weight of the patient and can be administered one or more times per day. Anti-HIV anionic oligomers can be administered with a pharmaceutical carrier using conventional dosage unit forms either orally or parenterally.

For oral administration, anti-HIV anionic oligomers can be formulated into solid or liquid preparations such as capsules, pills, tablets, troches, lozenges, melts, powders, solutions, suspensions, or emulsions. The solid unit dosage forms can be a capsule which can be of the ordinary hard- or soft-shelled gelatin type containing, for example, surfactants, lubricants, and inert fillers such as lactose, sucrose, sorbitol, calcium phosphate, and cornstarch. In another embodiment the anionic oligomers of this invention can be tableted with conventional tablet bases such as lactose, sucrose, and cornstarch in combination with binders such as acacia, cornstarch, or gelatin, disintegrating agents intended to assist the break-up and dissolution of the tablet following administration such as potato starch, alginic acid, corn starch, and guar gum, lubricants intended to improve the flow of tablet granulations and to prevent the adhesion of tablet material to the surfaces of the tablet dies and punches, for example, talc, stearic acid, or magnesium, calcium, or zinc stearate, dyes, coloring agents, and flavoring agents intended to enhance the aesthetic qualities of the tablets and make them more acceptable to the patient. Suitable excipients for use in oral liquid dosage forms include diluents such as water and alcohols, for example, ethanol, benzyl alcohol, and the polyethylene glycols, either with or without the addition of a pharmaceutically-acceptable surfactant, suspending agent, or emulsifying agent.

The anti-HIV anionic oligomers of this invention may also be administered parenterally, that is, subcutaneously, intravenously, intramuscularly, or interperitoneally, as injectable dosages of the anionic oligomers in a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,3-dioxolane-4-methanol, ethers such as poly(ethyleneglycol) 400, an oil, a fatty acid, a fatty acid ester or glyceride, or an acetylated fatty acid glyceride with or without the addition of a pharmaceutically acceptable surfactant such as a soap or a detergent, suspending agent such as pectin, carbomers, methylcellulose, hydroxypropylmethylcellulose, or carboxymethylcellulose, or emulsifying agent and other pharmaceutical adjuvants.

Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum, and mineral oil. Suitable fatty acids include oleic acid, stearic acid, and isostearic acid. Suitable fatty acid esters are, for example, ethyl oleate and isopropyl myristate. Suitable soaps include fatty alkali metal, ammonium, and triethanolamine salts and suitable detergents include cationic detergents, for example, dimethyl dialkyl ammonium halides, alkyl pyridinium halides, and alkylamines acetates; anionic detergents, for example, alkyl, aryl, and olefin sulfonates, alkyl, olefin, ether, and monoglyceride sulfates, and sulfosuccinates; nonionic detergents, for example, fatty amine oxides, fatty acid alkanolamides, and polyoxyethylenepolypropylene copolymers; and amphoteric detergents, for example, alkyl-beta-aminopropionates, and 2-alkyl-imidazoline quarternary ammonium salts, as well as mixtures. The parenteral compositions of this invention will typically contain from about 0.5 to about 25% by weight of anti-HIV anionic oligomer in solution. Preservatives and buffers may also be used advantageously. In order to minimize or eliminate irritation at the site of injection, such compositions may contain a non-ionic surfactant having a hydrophile-lipophile balance (HLB) of from about 12 to about 17. The quantity of surfactant in such formulations ranges from about 5 to about 15% by weight. The surfactant can be a single component having the above HLB or can be a mixture of two or more components having the desired HLB. Illustrative of surfactants used in parenteral formulations are the class of polyethylene sorbitan fatty acid esters, for example, sorbitan monooleate.

The oligomers of this invention can also be used prophylactically, that is, to prevent transmission of virus from an infected individual to an uninfected target. Virus is spread proportionally via exchange of blood but may be transmitted via exchange of other bodily fluids as well. Thus the oligomers of this invention can be formulated with standard detergent products for use in cleaning, particularly in research and clinical laboratories and in hospitals where blood products of infected individuals are handled. Formulations containing the oligomers of the present invention can be used to clean medical/surgical equipment and utensils as well as the hands of and other skin areas of health care workers. The oligomers of this invention can also be applied, as a liquid or powder composition, to the surface of sexual prophylaxis such as condoms by either the user or manufacturer of the prophylaxis prior to sale. The oligomers of this invention can be formulated into a douche composition for use by females for use prior to subsequent sexual contact with an infected individual. The oligomers of this invention can also be formulated in lubricants and spermatacidal jellies and lotions. Finally, the oligomers of this invention can also be formulated as compositions to be added to hot tubs, whirlpool baths and swimming pools to inactivate potential virus activity.

Definitions

The terms used in the present application are defined as follows:

n represents the number average repeat length of the distribution through all formulae.

RPMI means a cell culture media.

TC ID50 means tissue culture infectious unit, i.e. the amount of culture fluid effective to infect 50% of the cells.

MTT means 3-(4,5-dimethylthiazol-2-yl)-2,5-diphenyltetrazolium bromide.

MT4 means a cell line.

P24 test-Abbott means an assay of the viral core antigen using the assay kit currently sold by Abbott.

Coulter™ HIV assay means a radioimmuno assay for P24 viral antigen determination.

rs $CD_4$ means recombinent soluble $CD_4$ comprised of the four extracytoplasmic immunoglobulin like variable (V) domains $V_1$–$V_4$.

T means 4-methylaniline or toluidine, except when using the term "T4 cells" or "T-helper cells".

P means phosgene.

C means p-cresol.

MBC means 4-methylbenzoyl chloride.

TPC means 1,4-benzenedicarbonyl chloride or terephthaloyl chloride.

TPCS means sodium 2,5-bis(chlorocarbonyl) benzenesulfonate, having the formula

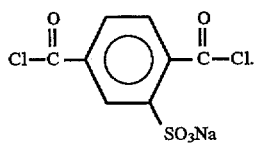

HBDS means dipotassium 2,5-dihydroxy-1,4-benzenedisulfonate, having the formula

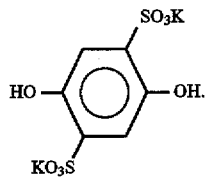

HBPDS means dipotassium 4,4'-dihydroxy(1,1'-biphenyl)-2,2'-disulfonate, having the formula

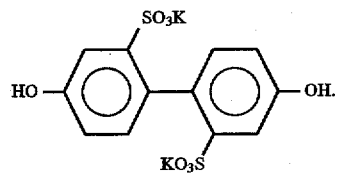

PDS means 2,5-diamino-1,4-benzenedisulfonic acid, having the formula

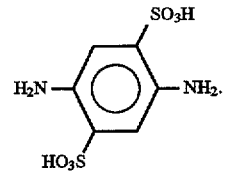

BPDS means 4,4'-diamino-(1,1'-biphenyl)-2,2'disulfonic acid, having the formula

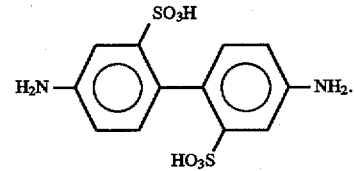

StDS means trans-2,2'-(1,2-ethenediyl)bis(5-aminobenzenesulfonic acid), having the formula

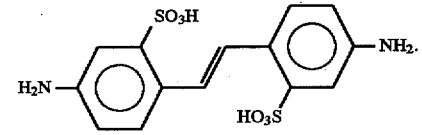

BPDS/P/T means poly{imino[2,2'-disulfo(1,1'-biphenyl)-4,4'-diyl]iminocarbonyl}, alpha-{[(4-methylphenyl)amino]carbonyl}-omega[(4-methylphenyl)amino]- and is represented by Formula I above when R is 4-methylphenyl, $R^2$ is hydrogen, X is

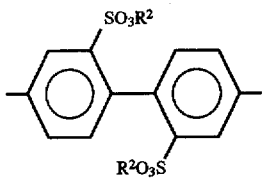

wherein n is defined as in Formula I.

StDS/P/T means poly[imino(3-sulfo-1,4-phenylene)-1,2-ethenediyl-(2-sulfo-1,4-phenylene)iminocarbonyl], alpha-{[(4-methylphenyl)aminocarbonyl}-omega-[(4-methylphenyl)amino- and is represented by Formula I above when R is 4-methylphenyl, $R^2$ is hydrogen, X is

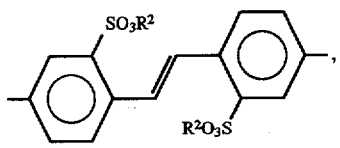

where n is defined as in Formula I.

PDS/P/T means poly[imino(2,5-disulfo-1,4-phenylene)iminocarbonyl], alpha-{[(4-methylphenyl)amino]carbonyl}-omega-[(4-methylphenyl)amino]- and is represented by Formula I above when R is 4-methylphenyl, $R^2$ is hydrogen, X is

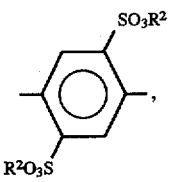

and n is defined as in Formula I.

HBDS/P/C means poly[oxy(2,5-disulfo-1,4-phenylene)oxycarbonyl], alpha-[(4-methylphenoxy)carbonyl]-omega-(4-methylphenoxy)- and is represented by Formula II above when $X^1$ is 4-methylphenyl, $R^2$ is hydrogen, X is

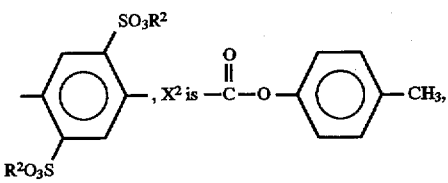

, $X^2$ is $-\overset{O}{\underset{\|}{C}}-O-\phantom{}-CH_3$, and n is defined as in Formula I.

HBPDS/P/C means poly{oxy[2,2'-disulfo(1,1'-biphenyl)-4,4'-diyl]oxy-carbonyl}, alpha-[(4-methylphenoxy)carbonyl]-omega-(4-methylphenoxy)- and is represented by Formula II above when $X^1$ is 4-methylphenyl, $R^2$ is hydrogen, X is

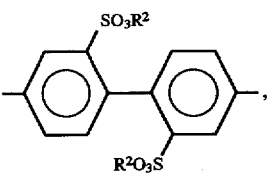

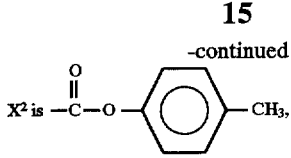

and n is defined as in Formula I.

HBPDS/TPC means poly{oxy[2,2'-disulfo(1,1'-biphenyl)-4,4'-diyl]oxy-carbonyl-1,4-phenylenecarbonyl}- and is represented by Formula III when $R^4$ and $R^5$ are hydrogen, $X^3$ is p-phenylene, X is

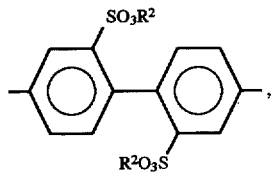

where n is defined as in Formula I.

HBDS/TPC means poly[oxy(2,5-disulfo-1,4-phenylene)oxycarbonyl-1,4-phenylenecarbonyl]- and is represented by Formula III when $R^4$ and $R^5$ are hydrogen, $X^3$ is p-phenylene, X is

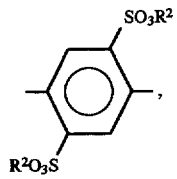

where n is defined as in Formula I.

BPDS/TPC/MBC means poly{imino[2,2'-disulfo(1,1'-biphenyl)-4,4'-diyl]iminocarbonyl-1,4-phenylenecarbonyl}, alpha-{[(4-methylphenyl)amino]carbonyl}-omega-[(4-methylphenyl)amino]- and is represented by Formula IV above when $R^6$ is R—C(O)—NH—X—NH—, R is 4-methylphenyl, $R^2$ is hydrogen, $R^7$ is 4-methylbenzoyl, $X^3$ is p-phenylene, X is

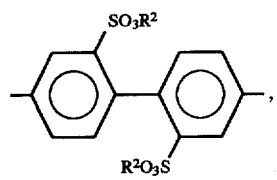

where n is defined as in Formula I.

The oligomers were prepared by modifying the procedure of Kershner (U.S. Pat. No. 4,895,660, the disclosure of which is hereby incorporated by reference, and described further below) by replacing a portion of one of the difunctional monomers with a mono-functional end-capping agent and running the reaction in the absence of a surfactant. The number average molecular weight ($M_n$) is governed by the stoichiometry of the reactants.

The oligomers of the present invention are prepared by the various reactions described below.

Polyureas and Polyamides (of Formulae I and III above)

The preferred process for the polyureas and polyamides of Formulae I and III above is described in the art (Kershner U.S. Pat. No. 4,824,916) and is further explained as follows. The various reactants and conditions are also described.

Diamines: A wide variety of aliphatic and aromatic diamines are included. The hydrocarbylene diradicals of which the diamines are composed can include methylene, ethylene, butylene, isopropylidene, phenylene, biphenylene, and other diradicals. The range of possible substituents is similarly broad, and includes hydroxyl, alkenyl, lower alkyl moieties, carboxylate, sulfonate, and halogens. The substituents are non necessarily anionic at neutral pH in water.

Difunctional Electrophiles: Phosgene (carbonyl dichloride), carbonyl dibromide, $Cl_3COCOCl$, $Cl_3COCO_2CCl_3$, diacid halides of aliphatic and aromatic dibasic acids such as oxalic, malonic, succinic, glutaric, adipic, sebacic, phthalic, isophthalic, 2,6-naphthalic acids.

Acid Acceptors: Several bases have been employed, such as sodium carbonate, sodium hydroxide, and tributylamine.

Miscellaneous additives: Various surfactants may be added. Suitable surfactants may be non-ionic, such as sorbitan monolaurate, sorbitan monostearate, ethylene glycol distearate, polyethylene oxy/polypropylene oxy polymer. Such surfactants can be difficult to remove from the product, and therefore the use of surfactants is not preferred.

Solvents: Single solvent process employ polar aprotic solvents such as N,N-dimethylacetamide and N,N-dimethylformamide. Also applicable are a combination of water and a second solvent, such as toluene, carbon tetrachloride, benzene, acetone, ethylene dichloride, and the like. Typical ratios of organic to aqueous solvents are about 0.5 to about 2.

In the processes described in the art, the diacid halide is added to a stirred solution or suspension of the other starting materials. In some instances the base is added during the carbonyl dihalide addition. The temperature is maintained between 0° and 50° C., preferably 20° to 30° C. A reactant ratio (molar ratio of diamine to diacid halide) from about 0.9 to 1.2 may be used, with essentially equimolar amounts preferred.

The reaction is stirred at a rate sufficient to achieve mixing of the reactants. The reaction rate is dependent in part on the interfacial area between the phases, and therefore vigorous stirring is preferable. A commercial blender may be employed for this purpose.

The process used to prepared the polyureas of the present invention is a modification of the process described above.

Diamines: The diamines of the present invention are primarily aromatic, with the formulas described in previous sections. Such diamines are substituted with at least one group which is charged at neutral pH, preferable sulfonate. Monovalent aliphatic substituents are allowable. A small set of aliphatic linking groups which tie aromatic radicals together may be used such as trans-substituted ethylene and acetylene. Preferred diamines are those in which the carbon-nitrogen bonds are forced to be parallel, such as PDS, BPDS, StDS, and 2,5-diaminobenzensulfonic acid.

Difunctional electrophiles: For the preparation of polyureas phosgene (carbonyl dichloride) and carbonyl dibromide, and other urea precursors such as carbonyl diimidazole, hexachloroacetone, $Cl_3COCO_2CCl_3$, $CCl_3COCl$, and $Cl_3OCOCl$ may be used. For the preparation of polyamides, aromatic diacids such as isophthalic and terephthalic acid (TPC), 2,6-napthalenedioic acid. These diacids may have neutral or charged substituents, such as monovalent alkyl radical (methyl, ethyl, butyl) and/or charged groups such as sulfonates, phosphates and the like. An example of such a charged difunctional electrophile is sodium 2,5-bis(chlorocarbonyl)benzenesulfonate (TPCS).

Acid Acceptors: A variety of inorganic bases may be used, such as alkali metal or divalent metal hydroxides carbonates, bicarbonates, phosphates. Acid acceptors with buffering capacity are preferred when all of the base is added prior to the addition of the difunctional electrophile. Organic bases such as trialkyl amines may be used, but are not preferred.

Monofunctional end capping agent: A variety of such molecular weight limiting agents may be used. Such agents may be aliphatic or aromatic compounds which react with the diamines or the difunctional electrophiles. Examples of suitable monofunctional agents are amines such as aniline, methylaniline, methylamine, ethylamine, butylamine, diethylamine, ammonia N-methylaniline, phenol and cresol Examples of monofunctional amine reactive agents are benzoyl chloride, methyl benzoyl chloride, acetyl chloride, and phenyl chloroformate. These end-capping agents may also contain charged substituents, for example potassium 2-sulfophenol or potassium 4-sulfoaniline.

Miscellaneous additives: The addition of surfactants is not necessary or preferred, and can complicate the isolation process.

Solvents: A single solvent, water, is preferred when the difunctional electrophile is a liquid at the reaction temperature. An example of such a difunctional electrophile is phosgene. When solid, water insoluble reactants are used, a small amount of a water immiscible cosolvent is desirable. For example, when terephthaloyl chloride is used a minimum amount of methylene chloride is added to improve the contact between the reactants. Example of such water immiscible cosolvents are chloroform, carbon tetrachloride, toluene, and methylene chloride. Typical ratios of organic to aqueous solvents are 0 to 1, with 0 to 0.1 preferred.

The process is conducted at temperatures which allow the reaction to proceed, typically from about 0° to 100° C. Preferable temperatures are 0° to 25° C. When low boiling starting materials are used, for example phosgene (bp 6° C.), it is advantageous to operate at temperatures at or below the boiling point. The pressure is not important and typically ambient pressure is employed. The pH of the reaction muss be carefully maintained for optimum process. At low pH (<6) the reaction is very slow, while at high pH (>10) the difunctional electrophile is unstable to attack by hydroxide or other base. Degradation of the polyurea can also occur at high pH. The pH is preferably maintained between 7 and 9.

When no end capping agent is used, molecular weight control can be achieved by careful adjustment of the stoichiometry of the reactants. Either the diamine or the difunctional electrophile may be used in excess, for example from 1 to 100% molar excess. This stoichiometry must account for any of the difunctional electrophile which is destroyed by hydrolysis prior to reaction with the diamine. For example, when phosgene is used at high pH, a large excess is required to compensate for the fast reaction with hydroxide which destroys it. Because the extent of this side reaction is difficult to control, a monofunctional end capping agent is preferably used to control the molecular weight. Although the techniques mentioned can be used to control the number average molecular weight, the products are mixtures of polymers with several molecular weights characterized by a distribution.

The order of addition of the reactants is not critical. However, the preferred order is to add the difunctional electrophile first. When acid acceptors which are not buffers are used, such as hydroxide, it is most preferable to add a portion at the beginning to achieve the desired pH, and then add the remainder concurrently with the difunctional electrophile.

Finally, it is desirable to conduct these polymerizations at high concentrations. This reduces the amount of solvent which must be removed to isolate the product. Also, in certain cases the product precipitates from the reaction solution near the end of the reaction, and may be isolated by simply decanting the solvent. Most of the inorganic salt which results from reaction of The acid acceptor is removed in this process. The concentration is not critical, and may be from 0.5 to 50 wt%, expressed as weight of diamine to weight of solvent. A preferred range is 5 to 20 wt%.

The product may be isolated by precipitation of the reaction solution into a solvent which is water miscible but is a poor solvent for the product. Examples of such solvents are acetone, methanol, ethanol, isopropanol.

Polycarbonates and Polyesters (of Formulae II and IV above).

The process previously described for the polyureas and polyamides was used, with the following exceptions: Diphenols were used in place of the diamines: Suitable aromatic diphenols containing at least one substituent which is anionic at pH 7. These diphenols have identical structures to those of the diamines except that the amines are replaced with hydroxyl groups. It is possible to pretreat the diols with one or two moles of base to form the mono- or diphenoxides. Some specific examples are dipotassium 4,4'-dihydroxy(1,1'-biphenyl)-2,2'-disulfonate (HBPDS) and dipotassium 2,5-dihydroxy-1,4-benzenedisulfonate (HBDS).

The process conditions are much more critical due to the instability of the products in aqueous solutions. Of particular importance is pH control. At pH levels below 7 the polymerization rate is very slow, while at high pH (>9) the carbonate or ester groups in the polymer undergo hydrolysis. A preferred pH range is 7 to 8, and it is desirable to have an automatic pH controller to maintain it. The useful range of temperatures under which the polymerization can be conducted is more narrow, 0° to 40° C., and preferably from 0° to 25° C.

After addition of the diacid chloride is complete, it is desirable to wait for a time, typically 15 to 120 minutes to insure that the conversion of starting materials is complete. Additional base may be added during this period, bus the pH is never allowed to rise above the previously described limits. The product is isolated as a distribution of products as described above.

The invention will be further clarified by a consideration of the following examples, which are intended to be purely exemplary of the present invention.

General Experimental

All solvents and reagents were obtained from commercial suppliers and used without further purification, except that BPDS was purified by recrystallizing from dimethyl sulfoxide under nitrogen atmosphere.

PDS was prepared by the procedure described in DE 1,393,557 (which disclosure is hereby incorporated by reference), and the product recrystalized from 1% (v/v) $H_2SO_4$.

The inherent viscosity was measured at 0.5 g/dL in deionized water and Hank's balanced salt solution (HBSS) (available from Sigma Chemical) at 25° C., unless noted otherwise.

The water content of the purified diamines was determined by Karl Fischer titration.

Proton and carbon nuclear magnetic resonance spectra were recorded on a Varian™ VXR 300 or an Varian™ Gemini 300 spectrometer. Samples were dissolved in D₂O, unless otherwise noted. Where possible the number average molecular weights of the oligomers was confirmed by integrating the area of the resonances from the methyl groups of the end caps relative to the aromatic resonances of the repeat unit. In many cases, particularly the polyamides prepared from BPDS or StDS and TPC, the resonances were too broad to be of value.

High pressure liquid chromatographic analysis (HPLC) were performed on an HP 1090 liquid chromatograph using a 200 mm×2.1 mm C-18 reverse phase column. The column was eluted with a gradient solution starting initially with of 35% of $CH_3CN$ and 65% of 5 mM tetra-n-butylammonium sulfate and ending with 55% $CH_3CN$ and 45% of tetra-n-butylammonium sulfate.

The phosgene reaction was carried out in a typical phosgenation apparatus having a stainless steel phosgene reservoir connected to a phosgene tank, nitrogen line and reaction feed line. The reservoir was mounted on a scale and could be filled directly from the phosgene tank when needed. The differential weight of the reservoir before and after the reaction was reported as the amount of phosgene added. Unless otherwise noted, a nitrogen carrier stream of 0.3 mL/min was maintained throughout the reaction. Phosgene was introduced at a rate of 0.9 mL/min (total gas flow of 1.2 mL/min during phosgene addition). In general a three-fold excess of phosgene was added to the reaction vessel. A stirring rate of 300 rpm was used and the solution maintained at 10° to 15° C. throughout the course of the reaction.

The products were routinely dried in a vacuum oven at 40°–50° C. for a minimum of 15 hours.

STARTING MATERIALS

Example A

Preparation of HBPDS, having the formula

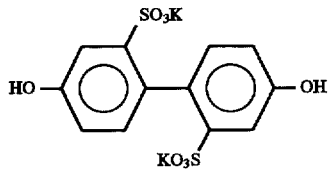

To a 2 L flask equipped with an addition funnel and magnetic stir bar was added 49.99 g (0.145 mol) of 4,4'-diamino(1,1'-biphenyl)-2,2'-disulfonic acid and 600 mL of water. The diamine was solubilized by the addition of 30 mL (0.15 mol) of 5M NaOH. To the resulting solution was added 20.56 g (0.298 mol) of sodium nitrite. The reaction mixture was then cooled to 0° C. and 60 mL of concentrated $H_2SO_4$ dissolved in 360 mL of water was added over 30 min. A yellow solid was formed. To the mixture was then added 300 mL of water and the mixture maintained at 0° C. for one hour. The reaction mixture was then filtered. The yellow solid was placed in a 1 L flask dissolved in 800 mL of water, and heated until about 50 mL of water remained. Nitrogen gas was evolved during heating. To the concentrated solution was added 20.14 g (0.146 mol) of $K_2CO_3$, followed by boiling the solution. Absolute ethanol (1.5 L) was then added, and a brown solid precipitated. The solid was filtered and dried overnight in a 50° C. oven. The product, HBPDS, was obtained in a yield of 32.33 g (53%), and further characterized by $^1$H NMR δ6.70 (dd, 1H), 7.05 (d, 1H), 7.14 (d, 1H).

Example B

Preparation of TPCS, having the formula

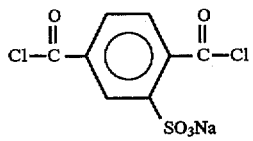

A 500 mL flask, equipped with a mechanical stirrer, thermometer and reflux condenser, was charged with 40.49 g (0.143 mol) of the monosodium salt of 2-sulfoterephthalic acid, 160 mL of chlorobenzene, 2.4 mL (0.031 mol) of dimethylformamide, and 23 mL (0.315 mol) of thionyl chloride. The solution was heated to 105° C. and stirred for 2 hours under nitrogen. During this time evolution of gas was noted. The solution was cooled to room temperature and a solid precipitated. The solid was filtered and dried overnight in a vacuum oven at room temperature. The product, as a pale yellow solid, was obtained in a yield of 20.56 g (47%).

To confirm the structure of the product, some of the product was converted to its methyl ester.

To a 25 mL flask, equipped with a magnetic stir bar and nitrogen bubbler, was added 0.9509 g (3.12 mmol) of the above product, 0.6874 g (6.47 mmol) of $Na_2CO_3$, and 10 mL of methanol. After stirring the reaction mixture overnight at room temperature under nitrogen, the solid was filtered, dried in a vacuum oven for 6 hours at room temperature, and determined that the dimethyl ester of the product had formed, being characterized by $^1$H NMR δ3.34 (s, 6H), 7.39 (d, 1H), 7.97 (d, 1H), 8.26 (s, 1H);

$^{13}$C NMR δ58.0, 136.0, 139.8, 140.9, 145.2, 146.8, 150.1, 183.5, 186.4.

FINAL PRODUCTS

EXAMPLE 1

Preparation of BPDS/P/T, having the formula

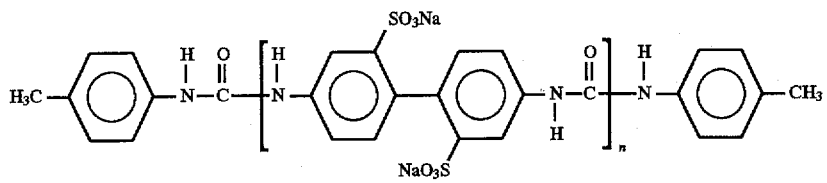

Oligomer A (n=6)

To a 1 L flask, equipped with a syringe port, thermometer well, pH electrode, dry-ice condenser, phosgene gas inlet tube, and a mechanical stirring device, was added 10.00 g (28.19 mmol) of BPDS, 1.35 g (9.40 mmol) of toluidine hydrochloride, and 400 mL of water. The reaction mixture was stirred and cooled to 12° C. The stirred suspension was then reacted with 13 mL of 5M NaOH until all the solids had dissolved. To the reaction mixture was then added 10.1 g (102 mmol) of phosgene over a 27 min period. During the phosgene addition, 5M NaOH was added with a syringe as necessary to maintain the pH between 7 to 8 (occasional extremes of pH 6 to 9 occurred). A total of 31 mL of NaOH was added. Stirring of the reaction mixture was continued for an additional 30 min, and then the pH was adjusted to 9.5 and the reaction mixture stirred for an additional 30 min. The reaction mixture was transferred to a 2 L flask and the crude product precipitated by the addition of 1000 mL of acetone. The crude product was filtered and air-dried to yield 18.6 g of an off-white powder having an $M_n$=2500. The inherent viscosity was 0.39 dL/g in $H_2O$, 0.15 dL/g in HBSS. The product was further characterized by $^1$H NMR δ2.2 (br s), 6.7–7.4 (m), 7.9–8.3 (m).

Oligomer B (n=9)

When the procedure of Example 1A was repeated using the following amounts of reagents:

| REAGENT | AMOUNT | mmol |
|---|---|---|
| BPDS | 12.06 g | 34.00 |
| T.HCl | 1.09 g | 7.56 |
| P | 11.0 g | 111.0 |
| Water | 400 mL | | the product, as a white powder, was obtained in a yield of 12 g and $M_n$=3600. The inherent viscosity was 0.52 dL/g in $H_2O$, 0.21 dL/g in HBSS.

Oligomer A (n=6)

When the procedure of Example 1A was repeated using the Following amounts of reagents:

| REAGENT | AMOUNT | mmol |
|---|---|---|
| StDS | 10.58 g | 28.00 |
| T.HCl | 1.34 g | 9.33 |
| P | 7.4 g | 74.8 |
| Water | 400 mL | | the product, as a yellow solid was obtained in a yield of 7.4 g and $M_n$=2600. Inherent viscosity was dL/g in $H_2O$. The product was further characterized by $^1$H NMR δ2.1 (br s), 6.7–8.1 (br m).

Oligomer B (n=9)

The procedure of Example 1A was repeated using the following amounts of reagents:

| REAGENT | AMOUNT | mmol |
|---|---|---|
| StDS | 10.58 g | 28.00 |
| T.HCl | 0.89 g | 6.22 |
| P | 9.0 g | 91.0 |
| Water | 400 mL | |

About one-half of the suspension obtained after addition of acetone was filtered due to frit clogging problems. The product, as a yellow solid, was obtained in a yield of 3.5 g and $M_n$=3800. Inherent viscosity was 0.18 dL/g in $H_2O$.

EXAMPLE 2

Preparation of StDS/P/T, having the formula

EXAMPLE 3

Preparation of PDS/P/T, having the formula

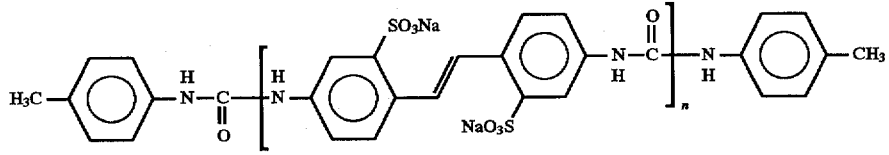

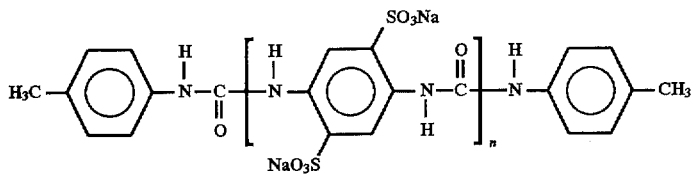

Oligomer A (n=9)

When the procedure of Example 1A was repeated using the following quantities of reagents:

| REAGENT | AMOUNT | mmol |
| --- | --- | --- |
| PDS | 3.50 g | 13.05 |
| T.HCl | 0.416 g | 2.90 |
| P | 4.3 g | 43.5 |
| Water | 225 mL | | the product, as a brown powder, was obtained in a yield of 2.95 g and $M_n$=2900. Inherent viscosity was 0.12 dL/g in $H_2O$ and 0.07 dL/g in HBSS. Oligomer B (n=15)

When the procedure of Example 1A was repeated using the following amounts of reagents:

| REAGENT | AMOUNT | mmol |
| --- | --- | --- |
| PDS | 3.50 g | 13.05 |
| T.HCl | 0.250 g | 1.74 |
| P | 4.2 g | 42.0 |
| Water | 225 mL | | the product, as a brown powder, was obtained in a yield of 3.83 g and $M_n$=4650. Inherent viscosity was 0.12 dL/g in $H_2O$ and 0.14 dL/g in HBSS

EXAMPLE 4

Preparation of HBDS/P/C, having the formula

Oligomer A (n=6)

To a 1 L flask, equipped with a syringe port, a thermometer well, mechanical stirrer, pH electrode, dry ice condenser, and a phosgene inlet tube, was added 10.16 g (29.35 mmol) of HBDS, 1.06 g (9.81 mmol) of p-cresol, and 400 mL of water. The reaction mixture was cooled to 10° C. with nitrogen flowing into the flask through the phosgene inlet. The stirred reaction mixture was treated with 5M sodium hydroxide until the pH of the solution was 8.0. To the reaction mixture was added 10.5 g (106.0 mmol) of phosgene over 35 min along with 42 mL of 5M sodium hydroxide as needed to maintain the pH of the solution between 7.0 to 7.5. After the phosgene addition was complete, the solution was allowed to stir for 20 min at 10° C. The dry ice was then removed from the condenser and the solution stirred an additional 30 min at 10° C. in order to allow the excess phosgene to evaporate. The aqueous solution was transferred to a 2 L flask and 100 mL of water used to rinse the reaction vessel was added. The product was precipitated by the addition of 1000 mL of acetone, filtered, and dried overnight in a vacuum oven at room temperature. The yield of product was 2.11 g, the inherent viscosity of the solid was 0.30 dL/g in $H_2O$, and $M_n$=2300.

EXAMPLE 5

Preparation of HBPDS/P/C, having the formula

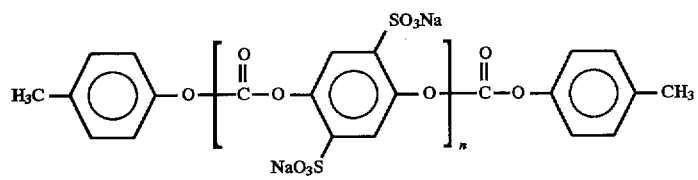

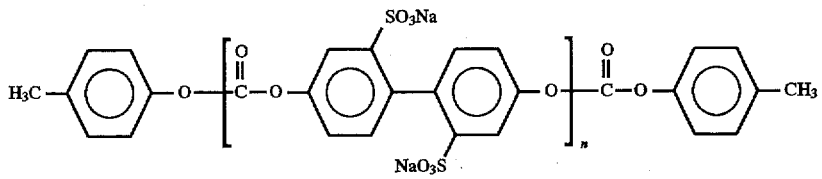

Oligomer A (n=6)

When the procedure of Example 4 was repeated using the following amounts of reagents:

| REAGENT | AMOUNT | mmol |
|---------|--------|------|
| HBPDS   | 12.35 g | 29.25 |
| p-cresol | 1.07 g | 9.91 |
| P       | 10.1 g | 102 |
| Water   | 400 mL | | the pH of the initial solution was 10.0 and was adjusted to pH 8.1 with concentrated hydrochloric acid. The phosgene was added over 32 min with 31 mL of 5M sodium hydroxide to maintain the pH between 7.5 and 8.0. After the phosgene was allowed to evaporate, the reaction mixture was transferred to a 2 L flask and 100 mL of water used to rinse the reaction vessel was added. The product was precipitated by the addition of 1400 mL of acetone, filtered, and dried overnight in a vacuum oven at room temperature. The yield of product was 1.89 g, the inherent viscosity of the solid was 0.17 dL/g in $H_2O$, and $M_n$=2700. The product was further characterized by $^1H$ NMR $\delta$2.2 (s), 7.0 (s), 7.2 (s), 7.5 (br s).

EXAMPLE 6

Preparation of HBPDS/TPC, having the formula

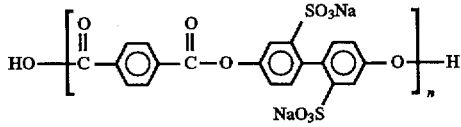

Oligomer A (n=4)

A 500 mL flask, equipped with a reflux condenser, addition funnel, and mechanical stirrer, was charged with 7.92 g (18.7 mmol) of HBPDS, 3.16 g (37.6 mmol) of sodium bicarbonate, 125 mL of water, and 25 mL of methylene chloride. To the stirred reaction mixture was added 3.80 g (18.7 mmol) of TPC in 100 mL of methylene chloride over one hour. The resulting solution was stirred for 1.5 hours at room temperature under nitrogen. The solution was then transferred to a 2 L flask and 100 mL of water used to rinse the reaction vessel was added. Acetone was added in 250 mL increments to break the emulsion. After 1000 mL of acetone was added, a solid was formed on the bottom of the flask which looked like beads filled with water. The solution was filtered, redissolved in 250 mL of water, precipitated with 750 mL of acetone, filtered, and dried overnight in a vacuum oven at room temperature. The brown solid weighed 4.89 g, the inherent viscosity of the solid was 0.16 dL/g in $H_2O$, and $M_n$=2100. The product was further characterized by $^1H$ NMR $\delta$2.2 (s), 7.0 (br s), 7.25 (br s), 7.5 (br s), 8.0 (br s).

EXAMPLE 7

Preparation of HBDS/TPC, having the formula

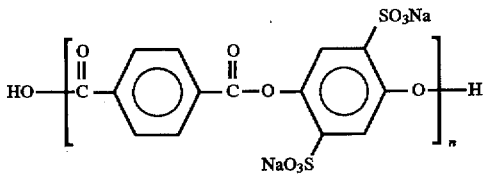

Oligomer A (n=3)

The procedure of Example 6 was repeated using the following amounts of reagents:

| REAGENT | AMOUNT | mmol |
|---------|--------|------|
| HBDS    | 6.51 g | 18.8 |
| NaHCO₃  | 3.15 g | 37.5 |
| CH₂Cl₂  | 125 mL | |
| TPC     | 3.84 g | 18.9 |
| Water   | 125 mL | |

The resulting solution was stirred for 1.5 hours at room temperature under nitrogen. The solution was then transferred to a 1 L flask and 100 mL of water used to rinse the reaction vessel was added. To the flask was added 450 mL of acetone to break the emulsion. There was a precipitate formed in the lower water layer. The solution was transferred to a separatory funnel and the lower layer separated. The water solution was then treated with 500 mL of acetone. A beige solid was formed, filtered, and dried over two days in a vacuum oven at room temperature. The product weighed 4.38 g, the inherent viscosity of the solid was 0.05 dL/g. Analysis by $^1H$ NMR and HPLC revealed significant amounts of starting diphenol.

In order to remove the unreacted starting material, 2.0 g of the above isolated solid was dissolved in 200 mL water. The product was precipitated by the addition of 700 mL of acetone, filtered, and dried overnight in a vacuum oven at room temperature. The solid product weighed 0.41 g, the inherent viscosity of the solid was 0.11 dL/g in $H_2O$, and $M_n$=1300.

EXAMPLE 8

Preparation of BPDS/TPC/MBC, having the formula

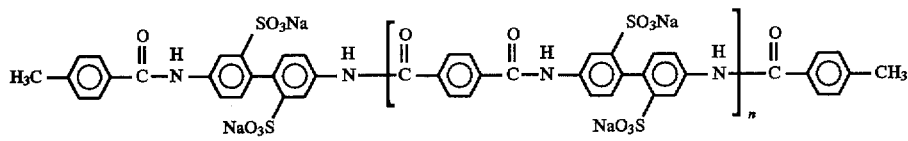

Oligomer A (n=6)

To a Waring blender was added 200 mL of deionized water and 2.65 g (25.0 mmol) of sodium carbonate and the mixture stirred at low speed until dissolved. To the reaction mixture was added 2.217 g (6.25 mmol) of BPDS via a powder addition funnel. The funnel was rinsed with 50 mL of water into the mixture. A clear colorless sodium salt solution was formed.

A second solution having 1.088 g (5.357 mmol) of TPC and 0.193 mL (236 mg, 1.786 mmol) of MBC in 200 mL of chloroform was prepared. The solution was immediately added in one portion to the sodium salt solution with vigorous stirring. The resultant white slurry was stirred at low speed for 15 min.

After sitting for 15 min, the slurry was transferred to a 2 L flask and the blender washed with about 200 mL of water which was added to the slurry. To the slurry was added 200 mL of acetone. The emulsion broke into a two-phase system with no visible precipitate. The lower layer was removed via separatory funnel; the upper layer was returned to the flask. To the flask was added 450 mL of acetone which effected precipitation. The precipitate was filtered through three layers of cheesecloth. The residual solvents were removed from the white gelatinous product by firmly squeezing the cheesecloth. The crude product was dissolved in 600 mL of water and reprecipitated by dilution to a total volume of 1600 mL with acetone. The precipitate was again collected, dissolved in 150 mL of water, and precipitated by adding 850 mL of acetone. The precipitate was collected as before, dried in a vacuum oven overnight at 35° to 36° C. to yield 0.8 g of a fibrous white product.

A second crop of product was obtained from the original mother liquor having a yield of 0.9 g. The combined solids were dissolved in 130 mL of water and precipitated by adding 500 mL of acetone to give 1.26 g, of a off-white solid, $M_n$=3450. Inherent viscosity was 3.85 dL/g in $H_2O$. The product was further characterized by $^1$H NMR δ2.1 (s), 7.44 (s), 7.78 (s), 8.02 (br s).

Oligomer B (n=3)

When the procedure of Example 8A was repeated using the following quantities of reagents:

| REAGENT | AMOUNT | mmol |
|---------|--------|------|
| BPDS    | 2.217 g | 6.25 |
| TPC     | 0.952 g | 4.688 |
| MBC     | 412 mg  | 3.125 |
| $Na_2CO_3$ | 2.65 g | | the product, as an off-white powder, was obtained in a yield of 1.58 g and $M_n$=2000. Inherent viscosity was 1.83 dL/g in $H_2O$ and 2.41 dL/g in HBSS.

Oligomer C (n=9)

When the procedure of Example 8A was repeated using the following quantities of reagents:

| REAGENT | AMOUNT | mmol |
|---------|--------|------|
| BPDS    | 2.217 g | 6.250 |
| TPC     | 1.142 g | 5.625 |
| MBC     | 165 mg  | 1.250 |
| $Na_2CO_3$ | 2.65 g | | the white, fibrous product, was obtained in a yield of 1.42 g and $M_n$=4900. Inherent viscosity was 4.23 dL/g in $H_2O$.

BIOLOGICAL DATA

Example I

ABILITY OF AN ANTI-HIV OLIGOMER TO PREVENT SYNCYTIA FORMATION AND EXPRESSION OF P24 VIRAL CORE ANTIGEN USING JM CELLS AND GB8 VIRUS STRAIN

To show that an oligomer of the invention blocks HIV infection, $CD4^+$ T-cells (JM) were exposed to a clinical isolate of HIV-I, GB8. The virus was first incubated with an oligomer for 15 minutes and then the cells were added. After 2 hours adsorption, the virus innoculum was removed and the cells were washed three times to remove traces of input virus. Antiviral activity was determined after 3 days incubation by plotting the mean number of syncytia found in quadruple cultures against $log_{10}$ concentration of anionic polymer or of other test compounds. The potency of an oligomer was also measured by assaying viral core antigen (P24 test-Abbott) in the supernatant fluid. Heparin, dextran sulfate, rs CD4, ATZ and/or ddC data, when included in any of the following Tables, are provided as positive controls.

TABLE I

| COMPOUND | CONC. µg/mL | SYNCYTIA | P24 (pg/mL) | % CONTROL |
|----------|-------------|----------|-------------|-----------|
| Control  | —           | +++      | >453600     | 100       |
| Heparin  | 5.0         | 0        | 2500        | <0.1      |
|          | 2.5         | +/0      | 25775       | <0.1      |
|          | 1.25        | +/0      | N.A.        | N.A.      |
|          | 0.6         | ++       | 44570       | 0.1       |
| Example 1A | 5.0       | 0        | N.D.        | N.A.      |
|          | 2.5         | 0        | 96          | <0.1      |
|          | 1.25        | 0        | 541         | <0.1      |
|          | 0.6         | +        | 37355       | 0.13      |
| Example 1B | 5.0       | 0        | 465         | <0.1      |
|          | 2.5         | 0        | 365         | <0.1      |
|          | 1.25        | +        | 35890       | <0.1      |
|          | 0.6         | +        | 32820       | 0.1       |

N.D. = not detected
N.A. = not assayed

Example II

Virus infection of JM cells was carried out in the presence of different concentrations of test compounds. JM cells ($1\times10^5$) and 50–100 syncytial forming units of virus (GB8) were added to duplicate wells of a tissue culture plate containing 1 mL volumes of growth medium with or without drug. The plate was incubated for 2 days at 37° C. and then scored for the presence of syncytia. At the same time the cells were washed and the growth medium replaced. After a further two days incubation, the cell free supernatant fluids were harvested and assayed for levels of P24 viral core antigen using the Coulter™ HIV Antigen assay. The results are given in Tables II–IV. In the Tables, N.D.=not detected and N.A.=not assayed.

TABLE II

| COMPOUND | CONC. µg/mL | SYNCYTIA (2 DAYS) | MEAN | % | P24 (units/mL) | % |
|---|---|---|---|---|---|---|
| Control | — | 39, 27, 42, 31, 42, 41, 51, 13, 57, 53, 56, 38, 41, 47, 41, 45, 52 | 42 | 100 | $3.6 \times 10^5$ | 100 |
| rs CD4 | 5 | 0 | 0 | 0 | $4.4 \times 10^4$ | 12 |
| Heparin | 10 | 0, 0 | 0 | 0 | $1.1 \times 10^4$ | 3 |
| | 3 | 0, 0 | 0 | 0 | $1.7 \times 10^4$ | 5 |
| | 1 | 2, 1 | 2 | 5 | $2.8 \times 10^4$ | 8 |
| | 0.3 | 21, 22 | 22 | 52 | $4.1 \times 10^4$ | 11 |
| | 0.1 | 28, 20 | 24 | 57 | N.A. | N.A. |
| | 0.03 | 39, 19 | 29 | 69 | N.A. | N.A. |
| | 0.01 | 33, 42 | 38 | 90 | N.A. | N.A. |
| Example 1A | 10 | 0, 0 | 0 | 0 | N.D. | N.D. |
| | 3 | 0, 0 | 0 | 0 | N.D. | N.D. |
| | 1 | 0, 0 | 0 | 0 | $9.1 \times 10^3$ | 3 |
| | 0.3 | 9, 19 | 14 | 33 | $4.0 \times 10^4$ | 11 |
| | 0.1 | 21, 28 | 25 | 58 | $4.0 \times 10^5$ | 100 |
| | 0.03 | 52, 52 | 52 | 123 | $4.3 \times 10^5$ | 100 |
| | 0.01 | 54, 66 | 60 | 143 | N.A. | N.A. |
| Example 1B | 10 | 0, 0 | 0 | 0 | N.D. | N.D. |
| | 3 | 0, 0 | 0 | 0 | N.D. | N.D. |
| | 1 | 0, 0 | 0 | 0 | $1.6 \times 10^3$ | 0.4 |
| | 0.3 | 2, 0 | 1 | 2 | $3.8 \times 10^4$ | 11 |
| | 0.1 | 36, 13 | 25 | 58 | $4.4 \times 10^5$ | 100 |
| | 0.03 | 43, 40 | 42 | 100 | $4.1 \times 10^5$ | 100 |
| | 0.01 | 40, 54 | 47 | 112 | N.A. | N.A. |
| Example 3A | 20 | 9, 1 | 5 | 12 | N.D. | N.D. |
| | 10 | 4, 2 | 3 | 7 | $4.1 \times 10^4$ | 11 |
| | 5 | 15, 14 | 15 | 36 | $3.6 \times 10^5$ | 100 |
| | 2.5 | 37, 38 | 38 | 90 | $2.5 \times 10^5$ | 69 |
| | 1.25 | 27, 13 | 20 | 48 | $4.3 \times 10^5$ | 100 |
| | 0.6 | 46, 55 | 51 | 120 | N.A. | N.A. |
| Example 8A | 100 | 0, 0 | 0 | 0 | N.D. | N.D. |
| | 30 | 0, 0 | 0 | 0 | N.D. | N.D. |
| | 10 | 0, 0 | 0 | 0 | N.D. | N.D. |
| | 3 | 0, 0 | 0 | 0 | $4.4 \times 10^4$ | 12 |
| | 1 | 2, 3 | 3 | 7 | $4.3 \times 10^4$ | 12 |

TABLE III

| COMPOUND | CONC. µg/mL | SYNCYTIA | MEAN | % | P24 (pg/mL) | % |
|---|---|---|---|---|---|---|
| Control | — | 46, 52, 69, 79, 84, 69, 81, 67, 68, 71, 64, 75 | 69 | 100 | 332300 | 100 |
| rsCD4 | 10 | 0, 0 | 0 | | 5340 | 1.6 |
| | 1 | 15, 24 | 20 | 28 | 88700 | 27 |
| | 0.1 | 35, 44 | 40 | 57 | 202000 | 61 |
| Heparin | 100 | 0, 0 | 0 | | 989 | 0.3 |
| | 10 | 0, 0 | 0 | | 70700 | 21 |
| | 1 | 9, 17 | 13 | 19 | 211000 | 63 |
| Example 8A | 500 | 0, 0 | 0 | | N.A. | N.A. |
| | 50 | 0, 0 | 0 | | 11600 | 3.5 |
| | 5 | 39, 31 | 35 | 51 | 268599 | 81 |

Example III
ABILITY OF VARIOUS ANTI-HIV OLIGOMERS TO PREVENT VIRUS-INDUCED CELL DEATH USING MT4 CELLS AND STRAIN RF.

Various oligomers were dissolved in RPMI and were then assayed for anti-HIV activity by making doubling dilutions of the solutions across a 96 well microtitre plate. To each well were then added $5 \times 10^4$ cells and 100 TCID50 of virus and the plates incubated at 37° C. for 7 days. MTT was added to each well and the plates incubated for a further 2 hours. The blue formazan crystals were dissolved using acidic isopropanol, and the absorbance measured at 540 nm. The results are given in Table IV.

TABLE IV

| COMPOUND | MW[a] | $ED_{50}$ µg/mL | $TD_{50}$ µg/mL |
|---|---|---|---|
| Heparin | 10,000–40,000 | 4.6 | >100 |
| Example 1B | 4,168 | 2.2 | >100 |
| Example 1A | 2,958 | 1.6 | >100 |
| Example 8C | 5,290 | 2.2 | >100 |
| Example 8A | 3,689 | 1.5 | >100 |
| Example 8B | 2,180 | 2.1 | >100 |
| Example 2B | 4,204 | 2.5 | >100 |
| Example 2A | 2,883 | 1.9 | >100 |
| Example 3B | 5,314 | 1.7 | >100 |
| Example 3A | 3,284 | >>10 | >100 |

[a]Number average molecular weight

Example IV

ABILITY TO PRETREAT CELLS WITH VARIOUS OLIGOMERS AND BLOCK HIV-I INFECTION USING JM CELLS AND GB8 STRAIN OF HIV-I

JM cells were pretreated overnight at 37° C. with different compounds at 20 µg/mL or left untreated. The cells were washed 3 times in RPMI medium and then infected with HIV-I (GB8) for 2 hours at room temperature. The cells were again washed 3 times in RPMI medium and resuspended in fresh medium prior to being distributed into duplicate wells and incubated at 37° C. After 2 days syncytia were scored and the cell free supernatant fluid harvested and assayed for P24 viral core antigen using the Coulter™ HIV antigen assay. The results are given in Table V.

TABLE V

| COMPOUND | MEAN SYNCYTIA | % | P24 (pg/mL) | % |
|---|---|---|---|---|
| Control | 119 | 100 | 28290 | 100 |
| Example 1A | 14 | 12 | 2623 | 9 |
| Example 1B | 52 | 44 | 2790 | 10 |
| Example 3A | 153 | 129 | 26880 | 95 |
| Heparin | 136 | 114 | 29090 | 103 |
| Dextran Sulfate | 184 | 155 | 28710 | 101 |

Example V

ABILITY OF AN ANTI-HIV-I OLIGOMER TO PREVENT SYNCYTIA FORMATION AND P24 VIRAL CORE ANTIGEN EXPRESSION BY DIFFERENT VIRAL STRAINS (GB8 AND RF) AND CELLS (JM AND C8166)

Cells were infected with strain RF or GB8 for 24 hours at 37° C. at a multiplicity of infection of 0.001. Cells were washed three times to remove residual virus and then replated into fresh growth medium. Cells were then treated for 24 and 48 hours post-infection (p.i.) with the indicated concentrations of test compounds. Syncytia and P24 antigen levels were determined on the indicated days p.i. by methods described before. Results are presented in Tables VI–VIII.

TABLE VI

EFFECT OF TREATING HIV-I (GB8) - INFECTED CELLS (JM) 24 HOURS POST-INFECTION

| COMPOUND | DOSAGE (μM) | TIME OF ADDITION POST-INFECTION (HOURS) | SYNCYTIA/WELL DAY 3 p.i.[a] | P24 pg/mL DAY 6 p.i.[a] | % CONTROL |
|---|---|---|---|---|---|
| Control | 0 | — | >100 | $1.03 \times 10^6$ | 100 |
| Example 1A | 2.5 | 0 | 0 | $4.2 \times 10^2$ | 0.04 |
| Example 1A | 2.5 | 24 | 0 | $1.21 \times 10^4$ | 1.2 |
| Example 1A | 1.2 | 24 | <10 | $1.5 \times 10^4$ | 1.5 |
| Example 1A | 0.62 | 24 | <20 | $5.6 \times 10^4$ | 5.4 |
| Example 1A | 0.31 | 24 | >50 | $1.65 \times 10^5$ | 16.0 |

[a]p.i. means post infection

The results in Table VI above indicate that events associated with viral induced cytopathological changes such as syncytia formation can be inhibited even when compounds are administered to previously infected cells. These results also indicate that the anionic oligomers are working by a mechanism in addition to blocking viral attachment to the CD4 cell surface protein.

The results in Table VII above indicate that the oligomers of this invention are effective against different viral strains and different cell types even when added 24 hours after virus infection.

TABLE VII

EFFECT OF TREATING HIV-I (RF) - INFECTED CELLS (C8166) 24 HOURS POST-INFECTION

| COMPOUND | DOSAGE (μM) | TIME OF ADDITION POST-INFECTION (HOURS) | SYNCYTIA/WELL DAY 2 | SYNCYTIA/WELL DAY 3 | P24 pg/mL DAY 6 p.i.[a] | % CONTROL |
|---|---|---|---|---|---|---|
| Control | 0 | — | + | +++ | $9.5 \times 10^5$ | 100. |
| ddC | 10 | 0 | 0 | 0 | $1.3 \times 10^4$ | 1.4 |
| ddC | 10 | 24 | + | +++ | $4.2 \times 10^5$ | 44.2 |
| AZT | 10 | 0 | 0 | 0 | $1.0 \times 10^4$ | 1.1 |
| AZT | 10 | 24 | + | ++ | $4.4 \times 10^4$ | 4.6 |
| Example 1A | 10 | 0 | 0 | 0 | $1.6 \times 10^4$ | 1.7 |
| Example 1A | 10 | 24 | 0 | 0 | $9.2 \times 10^3$ | 1.0 |
| Example 1A | 5 | 24 | 0 | 0 | $9.3 \times 10^3$ | 1.0 |
| Example 1A | 2.5 | 24 | 0 | 0 | $9.78 \times 104$ | 10.2 |
| Example 1A | 1.25 | 24 | 0 | ++ | $1.5 \times 10^6$ | 100. |
| Example 1A | 0.62 | 24 | + | +++ | $7.0 \times 10^5$ | 74. |

[a]p.i. means post infection

TABLE VIII

EFFECT OF TREATING HIV-I (GB8) - INFECTED CELLS (JM) 48 HOURS POST-INFECTION

| COMPOUND | DOSAGE (μM) | TIME OF ADDITION POST-INFECTION (HOURS) | SYNCYTIA/WELL DAY 3 p.i.[a] | DAY 6 p.i.[a] | P24 pg/mL | % CONTROL |
|---|---|---|---|---|---|---|
| Control | 0 | — | 69<br>61<br>70 | Cells Degenerated | $1.1 \times 10^5$ | 100. |
| Example 1A | 1.2 | 0 | 0 | 0 | $4.5 \times 10^2$ | 0.41 |

TABLE VIII-continued

EFFECT OF TREATING HIV-I (GB8) - INFECTED CELLS (JM)
48 HOURS POST-INFECTION

| COMPOUND | DOSAGE (μM) | TIME OF ADDITION POST-INFECTION (HOURS) | SYNCYTIA/WELL[b] DAY 3 p.i.[a] | DAY 6 p.i.[a] | P24 pg/mL | % CONTROL |
|---|---|---|---|---|---|---|
| Example 1A[b] | 1.2 | 48 | 0<br>0<br>19<br>10<br>12 | 0<br>0<br>2<br>5<br>9 | $2.1 \times 10^4$ | 19.0 |

[a]p.i. means post infection
[b]Approximately 50 syncytia/well were observed at 48 hours p.i. in the virus control wells. At this time, wells received 5 μg/mL of the oligomer of Example 1A and were incubated further. Syncytia were scored on day 3 p.i. At 4 days p.i. cells were washed in media containing 5 μg/mL of the oligomer of Example 1A and incubated further in 5 μg/mL of the oligomer of Example 1A. Virus control cells were washed in media as above without test compound and reincubated in parallel. On day 6 p.i. the cell-free media of all samples were collected and viral P24 antigen levels were determined.

The results of these studies show that the oligomers of Example 1A cleared cultures of syncytia, stabilized the infection and reduced virus antigen levels in cells having preestablished infections. Example VI Protocol: C8166 cells were infected with HIV (Strain RF) for 1 hour at room temperature to give a multiplicity of infection of approximately 0.01 infectious units per cell. The cells were washed three times and resuspended in fresh medium prior to being distributed into duplicate wells containing different concentrations of test compound. After 2 days at 37° the cells were observed for the presence of syncytia and the supernatant fluid assayed for p24 viral core antigen using the Coulter HIV antigen assay.

TABLE IX

Anti-HIV Activity of Various Phenyl and Biphenyl
Disulfonic Acid Polyester and Polycarbonate Oligomers

| COMPOUND | OLIGOMER CONC. μg/ml | SYNCYTIA Day 2 | p24 (pg/ml) Day 2 | % of VIRUS CONTROL |
|---|---|---|---|---|
| Virus Control | — | +++ | $3.2 \times 10^3$ | 100 |
| Example 6 | 100 | 0 | neg | 0 |
|  | 50 | 0 | neg | 0 |
|  | 25 | 0/+ | neg | 0 |
|  | 12 | 0/+ | neg | 0 |
| Example 4 | 100 | ++/+++ | $1.93 \times 10^3$ | 60 |
|  | 50 | ++/+++ | $2.82 \times 10^3$ | 88 |
|  | 25 | ++/+++ | $4.82 \times 10^3$ | 100 |
|  | 12 | ++/+++ | $3.05 \times 10^3$ | 95 |
| Example 7 | 100 | 0/+ | neg | 0 |
|  | 50 | ++ | $8.7 \times 10^2$ | 27 |
|  | 25 | ++/+++ | $1.45 \times 10^3$ | 45 |
|  | 12 | ++/+++ | $3.14 \times 10^3$ | 98 |
| Example 5 | 100 | +++ | $1.06 \times 10^3$ | 33 |
|  | 50 | +++ | $2.78 \times 10^3$ | 87 |
|  | 25 | +++ | $2.32 \times 10^3$ | 73 |
|  | 12 | +++ | $3.25 \times 10^3$ | 100 |
| AZT | 1 | 0 | neg | 0 |
|  | 0.1 | 0 | neg | 0 |
|  | 0.1 | 0/+ | neg | 0 |

Example VII

JM cells were infected with HIV (Strain GB8) to give approximately 200 syncytia/1×10⁵ cells after 3 days; virus infection was for 1 hour at room temperature. The cells were washed and resuspended in fresh medium before being distributed into duplicate wells of a tissue culture plate containing different concentrations of test compound. After 3 days the cells were observed, syncytia counted and the supernatant fluid assayed for p24 viral core antigen using the Coulter HIV Ag assay.

TABLE X

| COMPOUND | OLIGOMER Conc. μg/ml | MEAN SYNCYTIA 3 days p.i. | p24 pg/ml* 3 days p.i. |
|---|---|---|---|
| Virus Control | — | >200 | $5.2 \times 10^3$ |
| ddC | 10 | 0 | neg |
|  | 1 | 0 | neg |
|  | 0.1 | 2 | neg |
|  | 0.01 | 80 | $5.4 \times 10^3$ |
| Example 6 | 200 | 0 | — |
|  | 100 | 0 | neg |
|  | 50 | 12 | neg |
|  | 25 | 25 | $6.8 \times 10^3$ |
| Example 7 | 200 | 0 | neg |
|  | 100 | 7 | neg |
|  | 50 | 24 | neg |
|  | 25 | 43 | neg |
| Example 5 | 200 | 14 | neg |
|  | 100 | 22 | neg |
|  | 50 | 68 | neg |
|  | 25 | >200 | $6.7 \times 10^1$ |
| Example 4 | 200 | Toxic | — |
|  | 100 | Toxic | — |
|  | 50 | 64 | neg |
|  | 25 | 95 | $6.5 \times 10^3$ |

*supernatant fluids screened at 1/100 dilution.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

What is claimed is:

1. A method of treating an HIV infection in a patient in need thereof which comprises administering to the patient an effective amount of a pharmaceutical formulation comprising a pharmaceutically acceptable carrier and a rigid backbone, water soluable oligomer, having a molecular weight less than 10,000, recurring units coupled by carbonyl linking moieties, anionic groups and predominantly linear geometry in an aqueous medium and which is represented by any one of the following formula:

$$R-\left[\begin{array}{c}H\\|\\N-C\\||\\O\end{array}\right]_m\left[\begin{array}{cccc}H&&H&O\\|&&|&||\\N-X-N-C\end{array}\right]_n\begin{array}{c}H\\|\\N-R^3\end{array} \quad (I)$$

wherein:

R represents hydrogen, $C_1$–$C_4$ alkyl, phenyl, or phenyl substituted with from 1 to 2 $R^1$ moieties and up to 3 substituents independently selected from chloro, bromo or $C_1$–$C_4$ alkyl;

$R^1$ represents —$SO_3R^2$, —$CO_2R^2$, —$PO_3(R^2)_2$, or —$OPO_3R^2$;

$R^2$ represents hydrogen or a pharmaceutically-acceptable cation;

m is an integer 0 or 1, with the proviso that when m is O, R is hydrogen;

X represents

[structures of substituted phenyl groups with $R^1$ substituents in various positions]

[biphenyl and diphenylamide structures]

[structure with Y linker]

[stilbene structure]

[naphthalene structures with $R^1$ substituents] or ;

Y represents —$CO_2$—, —C≡C—, —N=N—, $$-\underset{\underset{O}{||}}{C}-\underset{\underset{H}{|}}{N}-, \quad -\underset{\underset{\downarrow}{}}{N}=N- \quad or \quad -\underset{\underset{R}{|}}{C}=N-N=\underset{\underset{R}{|}}{C}-;$$
$\quad\quad\quad\quad\quad\quad\quad\quad O$ n is an integer from 3 to 50; and $R^3$ represents —R or —X—$NH_2$, where R and X are defined as before;

B) a polycarbonate of the formula:

$$X^1-O-\left[\begin{array}{c}O\\||\\C-O-X-O\end{array}\right]_n-X^2 \quad (II)$$

wherein: X and n are defined as in Formula I, above; $X^1$ represents a HO—X—, where X is defined as in Formula I, above, $C_1$–$C_4$ alkyl, phenyl, or phenyl substituted with from 1 to 2 $R^1$ moieties and up to 3 substituents independently selected from chloro, bromo or $C_1$–$C_4$ alkyl; and $X^2$ represents hydrogen, or —$CO_2X^1$, where $X^1$ is defined as above;

C) a polyester of the formula $$R^4O-\left[\begin{array}{ccc}O&&O\\||&&||\\C-X^3-C-O-X-O\end{array}\right]_n-R^5 \quad (III)$$

wherein:

X and n are defined as in Formula I, above;

$R^4$ represents —$R^2$, as defined in Formula I, above, or —$X^1$, as defined in Formula II, above;

$R^5$ represents $$R^4O-\overset{O}{\underset{||}{C}}-X^3-\overset{O}{\underset{||}{C}}-;$$

where $R^4$ is defined as in Formula III, above, or —$R^2$, where $R^2$ is defined as in Formula I, above;

$X^3$ represents

[structures of substituted phenyl and biphenyl groups with $R^1$ substituents]

-continued

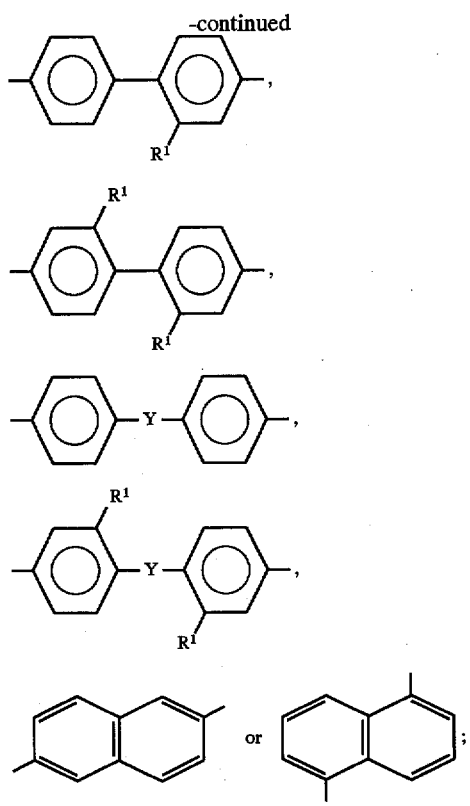

wherein $R^1$ and Y are defined as in Formula I, above; or

D) a polyamide of the formula:

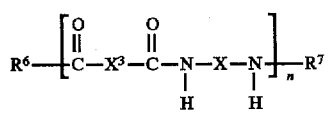

wherein:

X and n are defined as in Formula I, above;

$X^3$ is defined as in Formula III, above;

$R^6$ represents $H_2N$—X—NH—, $R^2O$—, RNH— or R—C(O)—NH—X—NH—, where R, $R^2$ and X are defined as in Formula I, above;

$R^7$ represents hydrogen,

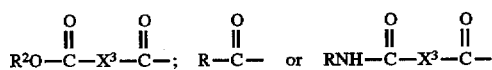

where

R and $R^2$ are defined as in Formula I, above; and $X^3$ is defined as in Formula III, above.

2. A method of treating an HIV infection in a patient in need thereof which comprises administering to the patient an effective amount of a pharmaceutical formulation of claim 1 wherein the oligomer is in the form of its pharmaceutically-acceptable salt.

3. A method of treating an HIV infection in a patient in need thereof which comprises administering to the patient an effective amount of a pharmaceutical formulation of claim 1 wherein the number average molecular weight of the oligomer is from about 500 to about 10,000.

4. A method of treating an HIV infection in a patient in need thereof which comprises administering to the patient an effective amount of a pharmaceutical formulation of claim 1 wherein the number average molecular weight of the oligomer is from about 1,000 to about 6,000.

5. A method of treating an HIV infection in a patient in need thereof which comprises administering to the patient an effective amount of a pharmaceutical formulation of claim 1 wherein the oligomer is a polyurea of Formula 1 wherein R and $R^3$ are 4-methylphenyl, m is 1, n is 3 to 15, X is

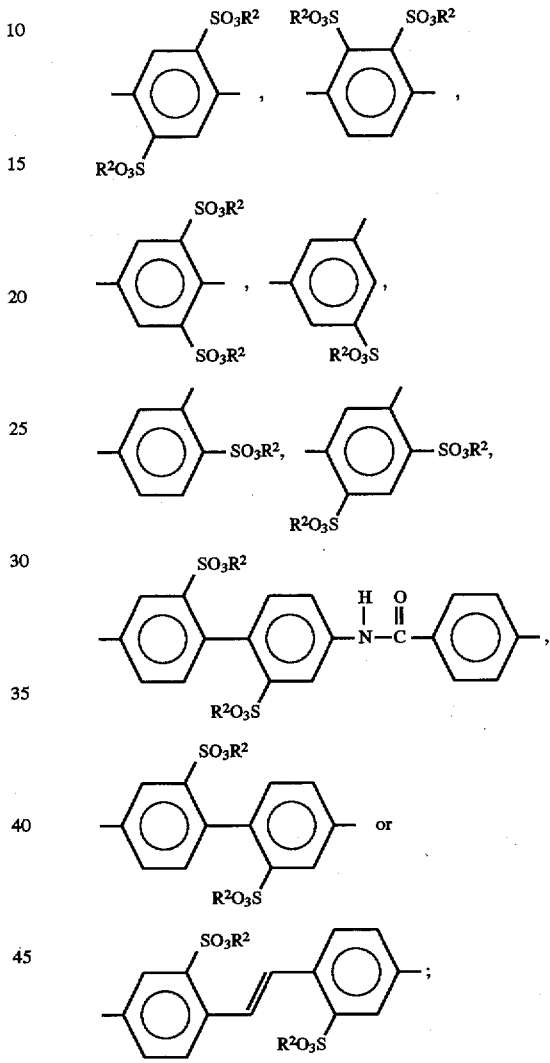

and $R^2$ is hydrogen or a pharmaceutically-acceptable cation.

6. A method of treating an HIV infection in a patient in need thereof which comprises administering to the patient an effective amount of a pharmaceutical formulation of claim 5 wherein the oligomer is of the formula:

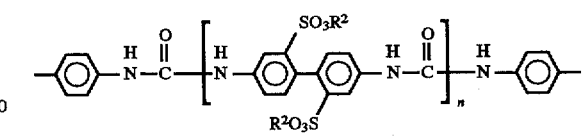

wherein n is 3–9.

7. A method of treating an HIV infection in a patient in need thereof which comprises administering to the patient an effective amount of a pharmaceutical formulation of claim 5 wherein the oligomer is of the formula:

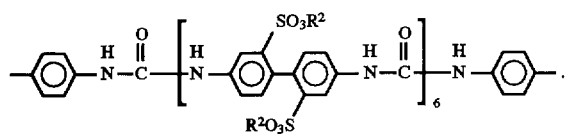

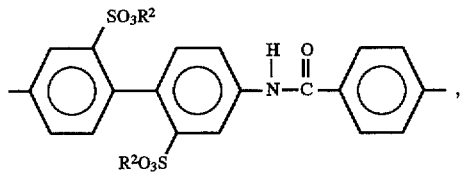

8. A method of treating an HIV infection in a patient in need thereof which comprises administering to the patient an effective amount of a pharmaceutical formulation of claim 5 wherein the oligomer is of the formula:

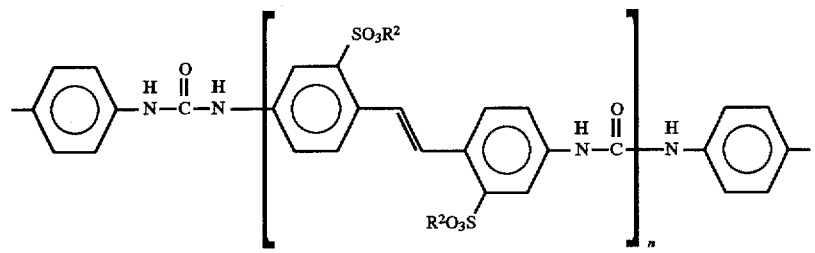

wherein n is 3–9.

9. A method of treating an HIV infection in a patient in need thereof which comprises administering to the patient an effective amount of a pharmaceutical formulation of claim 5 wherein the oligomer is of the formula:

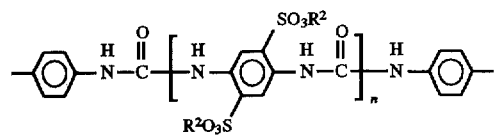

wherein n is 3–15.

10. A method of treating an HIV infection in a patient in need thereof which comprises administering to the patient an effective amount of a pharmaceutical formulation of claim 1 wherein the oligomer is a polycarbonate of Formula II wherein $X^1$ is a 4-methylphenyl; $X^2$ is —$CO_2$-(4-methylphenyl), n is 3 to 15 and X is:

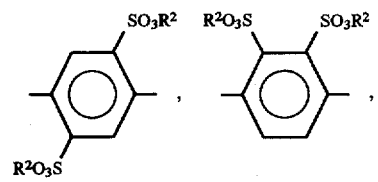

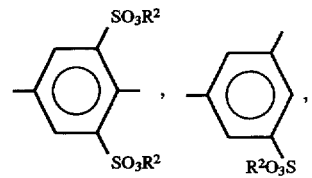

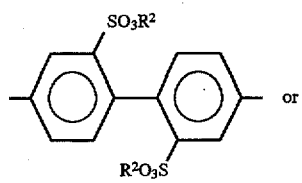

11. A method of treating an HIV infection in a patient in need thereof which comprises administering to the patient an effective amount of a pharmaceutical formulation of claim 10 wherein the oligomer is of the formula:.

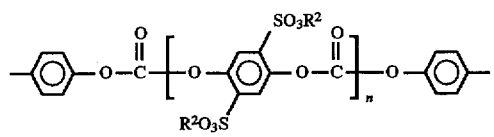

wherein n is 3–9.

12. A method of treating an HIV infection in a patient in need thereof which comprises administering to the patient an effective amount of a pharmaceutical formulation of claim 10 wherein the oligomer is of the formula:

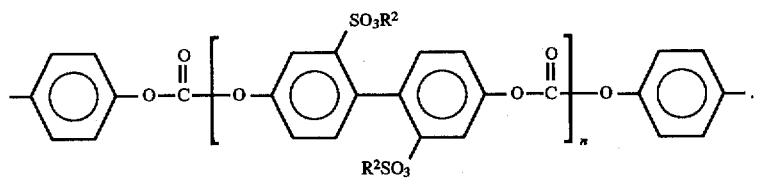

13. A method of treating an HIV infection in a patient in need thereof which comprises administering to the patient an effective amount of a pharmaceutical formulation of claim 1 wherein the oligomer is a polyester of Formula III wherein $R^4$ and $R^5$ are hydrogen, n is 3 to 15, $X^3$ represents

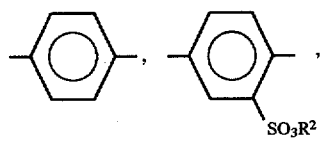

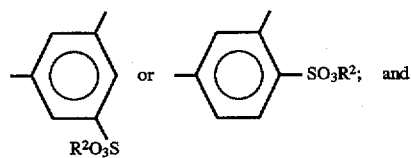; and and X represents

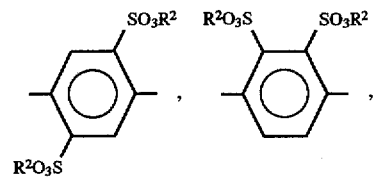

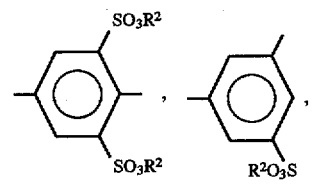

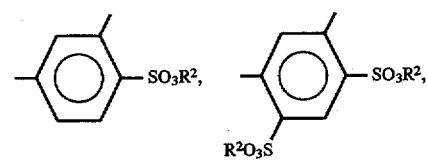

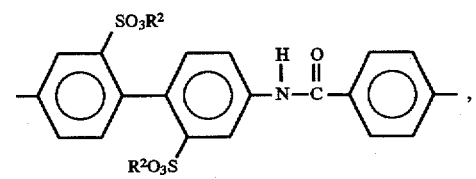

-continued

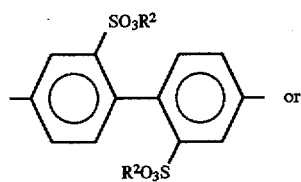 or

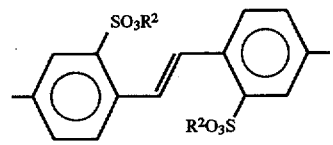

14. A method of treating an HIV infection in a patient in need thereof which comprises administering to the patient an effective amount of a pharmaceutical formulation of claim 13 wherein the oligomer is of the formula:

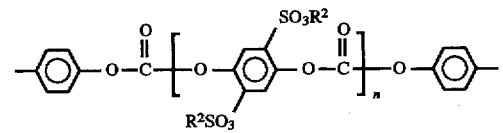

wherein n is 3–9.

15. A method of treating an HIV infection in a patient in need thereof which comprises administering to the patient an effective amount of a pharmaceutical formulation of claim 13 wherein the oligomer is of the formula:

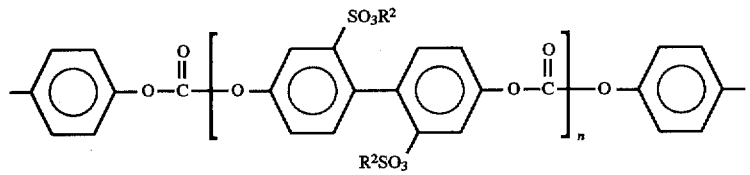

wherein n is 3–9.

16. A method of treating an HIV infection in a patient in need thereof which comprises administering to the patient an effective amount of a pharmaceutical formulation of claim 1 wherein the oligomer is a polyamide of Formula IV wherein $R^6$ is phenyl; $R^7$ is methyl benzoyl; n is 3 to 15; $X^3$ represents:

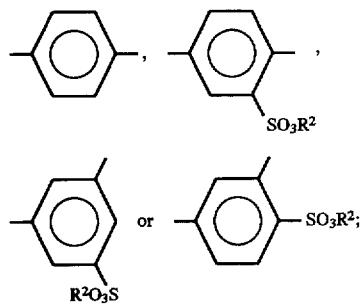

and X represents

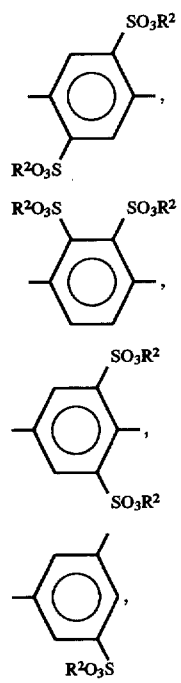

-continued

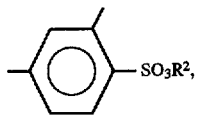

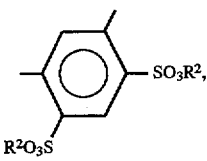

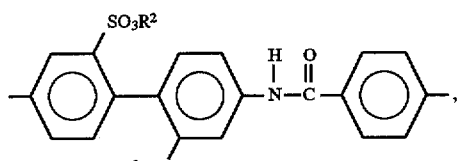

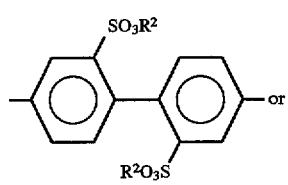

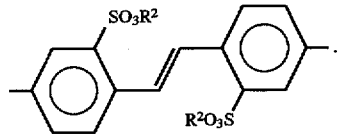

17. A method of treating an HIV infection in a patient in need thereof which comprises administering to the patient an effective amount of a pharmaceutical formulation of claim 16 wherein the oligomer is of the formula:

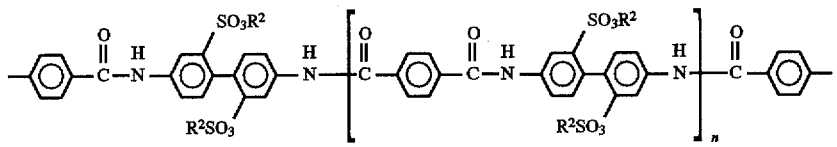

wherein n is 3–9.

18. A method of treating an HIV infection in a patient in need thereof which comprises administering to the patient an effective amount of a pharmaceutical formulation comprising a mixture of oligomers which are water soluble, have a rigid backbone, a molecular weight <10,000, and recurring units coupled by carbonyl linking moieties, and which have anionic groups and predominantly linear geometry in an aqueous medium and which are represented by, the formula:

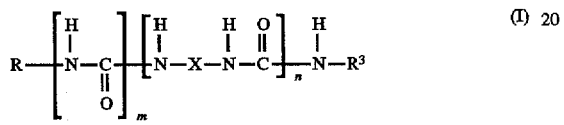

wherein:

R represents hydrogen, $C_1$–$C_4$ alkyl, phenyl, or phenyl substituted with from 1 to 2 $R^1$ moieties and up to 3 substituents independently selected from chloro, bromo or $C_1$–$C_4$ alkyl;

$R^1$ represents —$SO_3R^2$, —$CO_2R^2$, —$PO_3(R^2)_2$, or —$OPO_3R^2$;

$R^2$ represents hydrogen or a pharmaceutically acceptable cation;

m is an integer 0 or 1, with the proviso that when m is 0, R is hydrogen;

X represents:

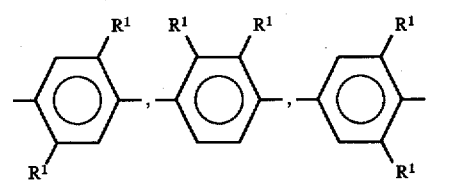

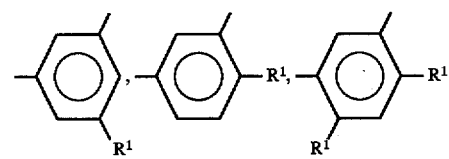

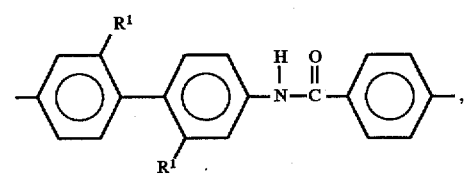

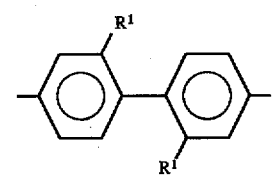

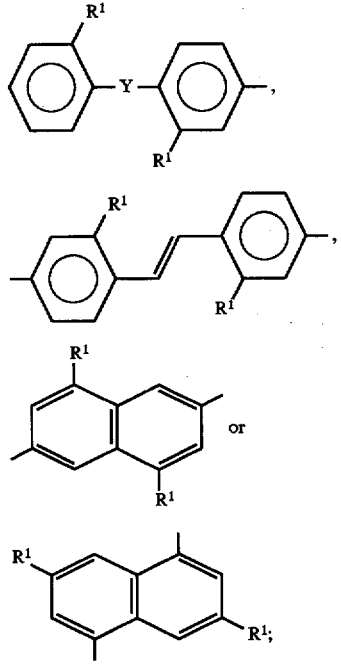

Y represents: —$CO_2$—, —C=C—, —N=N—,

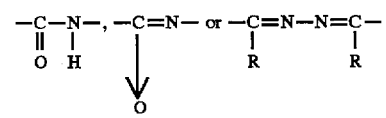

n is an integer from 3 to 50; and $R^3$ represents —R or —X—$NH_2$, where R and X are defined as before;

B) a polycarbonate of the formula:

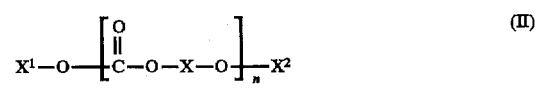

wherein:

X and n are defined as in Formula I, above;

$X^1$ represents HO—X—, where X is defined as in Formula I, above, $C_1$–$C_4$ alkyl, phenyl, or phenyl substituted with from 1 to 2$R^1$ moieties and up to 3 substituents independently selected from chloro, bromo or $C_1$–$C_4$ alkyl; and $X^2$ represents hydrogen or —$CO_2X^1$, where X is defined as above;

c) a polyester of the formula:

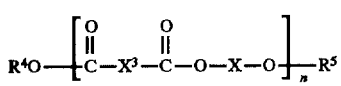  (III)

wherein

X and n are defined as in Formula I, above;

$R^4$ represents —$R^2$, as defined in Formula I, above, or $X^1$, as defined in Formula II, above;

$R^5$ represents

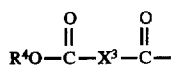

where $R^4$ is defined as in Formula III, above, or —$R^2$, where $R^2$ is defined as in Formula I, above;

$X^3$ represents

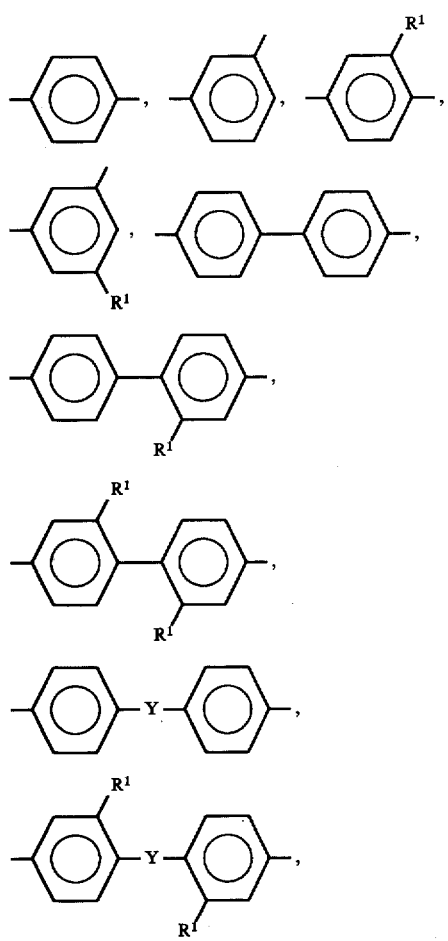

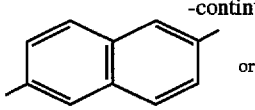

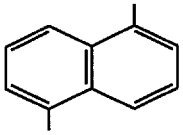

wherein $R^1$ and Y are defined as in Formula I, above; or

D) a polyamide of the formula:

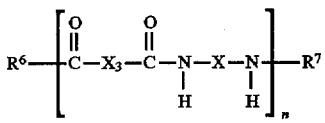  (IV)

wherein:

X and n are defined as in Formula I, above;

$X^3$ is defined as in Formula III, above;

$R^6$ represents $H_2N$—X—NH—, $R^2O$, RNH— or R—C(O)—NH—X—NH, wherein R, $R^2$ and X are defined as in Formula I, above;

$R^7$ represents hydrogen,

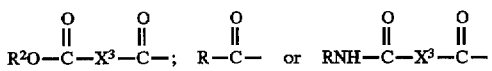

where

R ans $R^2$ are defined as in Formula I, above; and $X^3$ is defined as in Formula III, above.

19. A method of treating an HIV infection in a patient in need thereof which comprises administering to the patient an effective amount of a pharmaceutical formulation comprising a pharmaceutically acceptable carrier and a water-soluble, rigid backbone oligomer having a molecular weight less than 10,000 comprising recurring units coupled by carbonyl linking moieties, anionic groups and predominantly linear geometry such that regular spacing between the anionic groups exists in an aqueous medium.

20. The method of claim 19 wherein the oligomer is in the form of its salt.

21. The method of claim 20 wherein the salt is a pharmaceutically-acceptable salt.

22. The method of claim 19 wherein the oligomer is a polyurea, polycarbonate, polyester or polyamide.

23. The method of claim 22 wherein the recurring unit of the oligomer has two or more anionic groups.

24. The method of claim 23 wherein the oligomer is in the form of its salt.

25. The method of claim 24 wherein the salt is pharmaceutically-acceptable.